(12) United States Patent
McIntyre et al.

(10) Patent No.: US 7,680,526 B2
(45) Date of Patent: Mar. 16, 2010

(54) SYSTEM AND METHOD FOR OBTAINING A VOLUME OF INFLUENCE BASED ON NON-UNIFORM TISSUE CONDUCTIVITY DATA

(75) Inventors: Cameron C. McIntyre, Cleveland, OH (US); Christopher R. Butson, Shaker Heights, OH (US); John D. Hall, Mayfield Heights, OH (US); Jaimie M. Henderson, Stanford, CA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 12/008,760

(22) Filed: Jan. 14, 2008

(65) Prior Publication Data

US 2008/0114579 A1 May 15, 2008

Related U.S. Application Data

(62) Division of application No. 10/885,982, filed on Jul. 7, 2004, now Pat. No. 7,346,382.

(51) Int. Cl.
*G06T 17/20* (2006.01)

(52) U.S. Cl. .............. 600/416; 600/408; 600/410; 600/544; 382/128; 607/116; 345/420

(58) Field of Classification Search .............. 600/407, 600/408, 410, 416, 544; 607/2, 45, 99, 155, 607/116, 148; 382/128, 130; 345/420–423; 702/150–153

See application file for complete search history.

(56) References Cited

U.S. PATENT DOCUMENTS 4,341,221 A 7/1982 Testerman
(Continued)

FOREIGN PATENT DOCUMENTS

EP 1372780 A2 10/2002
(Continued)

OTHER PUBLICATIONS

""BioPSE" The Biomedical Problem Solving Environment", http://www.sci.utah.edu/cibc/software/index.html, NCRR Center for Integrative Biomedical Computing,(2004).
(Continued)

*Primary Examiner*—Brian Casler
*Assistant Examiner*—Parikha S Mehta
(74) *Attorney, Agent, or Firm*—Kenyon & Kenyon LLP

(57) ABSTRACT

This document discusses, among other things, brain stimulation models, systems, devices, and methods, such as for deep brain stimulation (DBS) or other electrical stimulation. A model computes a volume of influence region for a simulated electrical stimulation using certain stimulation parameters, such as amplitude, pulsewidth, frequency, pulse morphology, electrode contact selection or location, return path electrode selection, pulse polarity, etc. The model uses a non-uniform tissue conductivity. This accurately represents brain tissue, which has highly directionally conductive neuron pathways yielding a non-homogeneous and anisotropic tissue medium. In one example, the non-uniform tissue conductivity is obtained from diffusion tensor imaging (DTI) data. In one example, a second difference of an electric potential distribution is used to define a volume of activation (VOA) or similar volume of influence. In another example, a neuron or axon model is used to calculate the volume of influence without computing the second difference of the electric potential distribution.

28 Claims, 10 Drawing Sheets
(1 of 10 Drawing Sheet(s) Filed in Color)

U.S. PATENT DOCUMENTS

| | | | |
|---|---|---|---|
| 5,344,438 | A | 9/1994 | Testerman et al. |
| 5,560,360 | A | 10/1996 | Filler et al. |
| 5,938,688 | A | 8/1999 | Schiff |
| 6,146,390 | A | 11/2000 | Heilbrun et al. |
| 6,301,492 | B1 | 10/2001 | Zonenshayn |
| 6,343,226 | B1 | 1/2002 | Sunde et al. |
| 6,421,566 | B1 | 7/2002 | Holsheimer |
| 6,539,263 | B1 | 3/2003 | Schiff et al. |
| 6,560,490 | B2 | 5/2003 | Grill et al. |
| 6,675,046 | B2 | 1/2004 | Holsheimer |
| 2002/0062143 | A1 | 5/2002 | Baudino et al. |
| 2002/0123780 | A1 | 9/2002 | Grill et al. |
| 2002/0128694 | A1 | 9/2002 | Holsheimer |
| 2004/0044378 | A1 | 3/2004 | Holsheimer |
| 2004/0044379 | A1 | 3/2004 | Holsheimer |
| 2005/0033380 | A1 | 2/2005 | Tanner et al. |
| 2005/0070781 | A1 | 3/2005 | Dawant et al. |
| 2005/0085714 | A1 | 4/2005 | Foley et al. |
| 2005/0267347 | A1 | 12/2005 | Oster |
| 2006/0017749 | A1 | 1/2006 | McIntyre et al. |
| 2007/0288064 | A1 | 12/2007 | Butson et al. |

FOREIGN PATENT DOCUMENTS

| | | |
|---|---|---|
| WO | WO-02065896 A2 | 8/2002 |
| WO | WO-03086185 A1 | 10/2003 |
| WO | WO-2006017053 A1 | 2/2006 |

OTHER PUBLICATIONS

"U.S. Appl. No. 10/885,982, Final Office Action mailed Aug. 9, 2007", 8 pgs.

"U.S. Appl. No. 10/885,982, Final Office Action mailed Dec. 12, 2006", 10 pgs.

"U.S. Appl. No. 10/885,982, Non-Final Office Action mailed Apr. 19, 2007", 17 pgs.

"U.S. Appl. No. 10/885,982, Non-Final Office Action mailed Apr. 21, 2006", 20 pgs.

"U.S. Appl. No. 10/885,982, Response filed Mar. 12, 2007 to Final Office Action mailed Dec. 12, 2006", 26 pgs.

"U.S. Appl. No. 10/885,982, Response filed Jul. 19, 2007 to Non-Final Office Action mailed Apr. 19, 2007", 19 pgs.

"U.S. Appl. No. 10/885,982, Response filed Jul. 21, 2006 to Non-Final Office Action mailed Apr. 21, 2006", 24 pgs.

Et al., "Deep-brain stimulation of the subthalamic nucleus or the pars interna of the globus pallidus in Parkinson's disease", *N Engl J Med.*, 345(13), Author: Deep-Brain Stimulation for Parkinson's Disease Study Group,(Sep. 27, 2001),956-963.

"International Search Report and Written Opinion for for Application No. PCT/US2005/023672, date mailed Jan. 20, 2006", 19 Pages.

"Notice of Allowance Mailed Oct. 5, 2007 in U.S. Appl. No. 10/885,982", NOAR,8.

Adler, D E., et al., "The tentorial notch: anatomical variation, morphometric analysis, and classification in 100 human autopsy cases", *J. Neurosurg.*, 96(6), (Jun. 2002), 1103-1112.

Alexander, D C., et al., "Spatial transformations of diffusion tensor magnetic resonance images", *IEEE Transactions on Medical Imaging*, 20(11), (2001),1131-1139.

Alo, K. M., et al., "New trends in neuromodulation for the management of neuropathic pain", *Neurosurgery*, 50(4), (Apr. 2002),690-703; discussion 703-4.

Andrews, R. J., "Neuroprotection trek—the next generation: neuromodulation I. Techniques—deep brain stimulation, vagus nerve stimulation, and transcranial magnetic stimulation.", *Ann N Y Acad Sci.*, 993 (May 2003),1-13.

Andrews, R. J., "Neuroprotection trek—the next generation: neuromodulation II. Applications—epilepsy, nerve regeneration, neurotrophins.", *Ann N Y Acad Sci.*, 993, (May 2003),14-24.

Ashby, P , et al., "Neurophysiological effects of stimulation through electrodes in the human subthalamic nucleus", *Brain*, 122 ( Pt 10), (Oct. 1999),1919-1931.

Astrom, M. , et al., "The effect of cystic cavities on deep brain stimulation in the basal ganglia: a simulation-based study", *J Neural Eng.*, 3(2), (Jun. 2006),132-8.

Back, C. , et al., "Postoperative Monitoring of the Electrical Properties of Tissue and Electrodes in Deep Brain Stimulation", *Neuromodulation*, 6(4), (Oct. 2003),248-253.

Baker, K. B., et al., "Evaluation of specific absorption rate as a dosimeter of MRI-related implant heating", *J Magn Reson Imaging.*, 20(2), (Aug. 2004),315-20.

Baker, K. B., et al., "Subthalamic nucleus deep brain stimulus evoked potentials: Physiological and therapeutic implications", *Movement Disorders*, 17(5), (Sep./Oct. 2002),969-983.

Bammer, R , et al., "Diffusion tensor imaging using single-shot SENSE-EPI", *Magn Reson Med.*, 48(1), (Jul. 2002),128-136.

Basser, P J., et al., "MR diffusion tensor spectroscopy and imaging", *Biophys J.*, 66(1), (Jan. 1994),259-267.

Basser, P J., et al., "New currents in electrical stimulation of excitable tissues", *Annu Rev Biomed Eng.*, 2, (2000),377-397.

Bedard, C. , et al., "Modeling extracellular field potentials and the frequency-filtering properties of extracellular space", *Biophys J.*, 86(3), (Mar. 2004),1829-42.

Benabid, A L., et al., "Chronic electrical stimulation of the ventralis intermedius nucleus of the thalamus as a treatment of movement disorders", *J. Neurosurg.*, 84(2), (Feb. 1996),203-214.

Benabid, A L., et al., "Combined (thalamotoy and stimulation) stereotactic surgery of the VIM thalamic nucleus for bilateral Parkinson disease", *Appl Neurophysiol*, vol. 50, (1987),344-346.

Benabid, A. L., et al., "Future prospects of brain stimulation", *Neurol Res.*, 22(3), (Apr. 2000),237-46.

Benabid, A L., et al., "Long-term suppression of tremor by chronic stimulation of the ventral intermediate thalamic nucleus", *Lancet*, 337(8738), (Feb. 16, 1991),403-406.

Brummer, S. B., et al., "Electrical Stimulation with Pt Electrodes: II—Estimation of Maximum Surface Redox (Theoretical Non-Gassing) Limits", *IEEE Transactions on Biomedical Engineering*, vol. BME-24, Issue 5, (Sep. 1977),440-443.

Butson, Christopher R., et al., "Deep Brain Stimulation of the Subthalamic Nucleus: Model-Based Analysis of the Effects of Electrode Capacitance on the Volume of Activation", *Proceedings of the 2nd International IEEE EMBS*, (Mar. 16-19, 2005),196-197.

Butson, C. R., et al., "Deep brainstimulation interactive visualization system", *Society for Neuroscience*, vol. 898.7, (2005).

Butson, Christopher R., et al., "Patient-specific analysis of the volume of tissue activated during deep brain stimulation", *NeuroImage*, vol. 34, (2007),661-670.

Butson, C. R., et al., "Patient-specific models of deep brain stimulation: 3D visualization of anatomy, electrode and volume of activation as a function of the stimulation parameters.", *Soc Neurosci Abstr. 30*, (2004),1011.11.

Butson, C. R., et al., "Role of electrode design on the volume of tissue activated during deep brain stimulation", *J Neural Eng.*, 3(1), (Mar. 2006),1-8.

Butson, Christopher R., et al., "Sources and effects of electrode impedance during deep brain stimulation", *Clinical Neurophysiology*, vol. 117, (2006),447-454.

Butson, C. R., et al., "StimExplorer: Deep brain stimulation parameter selection software system", *In: Neuromodulation.*, DE Sakas, B Simpson and E Krames (eds), Springer-Verlag.,(2006),569-574.

Butson, Christopher R., et al., "Tissue and electrode capacitance reduce neural activation volumes during deep brain stimulation", *Clinical Neurophysiology*, vol. 116, (2005),2490-2500.

Christensen, Gary E., et al., "Volumetric transformation of brain anatomy", *IEEE Transactions on Medical Imaging*, 16(6), (Dec. 1997),864-877.

Cooper, S , et al., "Differential effects of thalamic stimulation parameters on tremor and paresthesias in essential tremor", *Movement Disorders*, 17(Supp. 5), (2002),S193.

Coubes, P , et al., "Treatment of DYT1-generalised dystonia by stimulation of the internal globus pallidus", *Lancet*, 355(9222), (Jun. 24, 2000),2220-2221.

Dasilva, A.F. M., et al., "A Primer Diffusion Tensor Imaging of Anatomical Substructures", *Neurosurg. Focus*; 15(1), (Jul. 2003),1-4.

Dawant, B. M., et al., "Compuerized atlas-guided positioning of deep brain stimulators: a feasibility study", *Biomedical Image registration, Second International Workshop, WBIR 2003.*, Revised Papers (Lecture notes in Comput. Sci. vol. (2717), Springer-Verlag Berlin, Germany,(2003),142-150.

Finnis, K. W., et al., "3-D functional atalas of subcortical structures for image guided stereotactic neurosurgery", *Neuroimage*, vol. 9, No. 6, Iss. 2, (1999),S206.

Finnis, K. W., et al., "3D Functional Database of Subcortical Structures for Surgical Guidance in Image Guided Stereotactic Neurosurgery", *Medical Image Computing and Computer-Assisted Intervention—MICCAI'99, Second International Conference*, Cambridge, UK, Sep. 19-22, 1999, Proceedings, (1999),758-767.

Finnis, K. W., et al., "A 3-Dimensional Database of Deep Brain Functional Anatomy, and Its Application to Image-Guided Neurosurgery", *Proceedings of the Third International Conference on Medical Image Computing and Computer-Assisted Intervention, Lecture Notes In Computer Science*; vol. 1935, (2000),1-8.

Finnis, K. W., et al., "A functional database for guidance of surgical and therapeutic procedures in the deep brain", *Proceedings of the 22nd Annual International Conference of the IEEE Engineering in Medicine and Biology Society*, vol. 3, (2000),1787-1789.

Finnis, K. W., et al., "Application of a Population Based Electrophysiological Database to the Planning and Guidance of Deep Brain Stereotactic Neurosurgery", *Proceedings of the 5th International Conference on Medical Image Computing and Computer-Assisted Intervention-Part II, Lecture Notes In Computer Science*; vol. 2489, (2002),69-76.

Finnis, K. W., et al., "Subcortical physiology deformed into a patient-specific brain atlas for image-guided stereotaxy", *Proceedings of SPIE*—vol. 4681 Medical Imaging 2002: Visualization, Image-Guided Procedures, and Display, (May 2002),184-195.

Finnis, Krik W., et al., "Three-Dimensional Database of Subcortical Electrophysiology for Image-Guided Stereotatic Functional Neurosurgery", *IEEE Transactions on Medical Imaging*, 22(1), (Jan. 2003),93-104.

Foster, K. R., et al., "Dielectric properties of tissues and biological materials: a critical review.", *Crit Rev Biomed Eng.*, 17(1), (1989),25-104.

Gabriels, L , et al., "Deep brain stimulation for treatment-refractory obsessive-compulsive disorder: psychopathological and neuropsychological outcome in three cases", *Acta Psychiatr Scand.*, 107(4), (2003),275-282.

Gabriels, L A., et al., "Long-term electrical capsular stimulation in patients with obsessive-compulsive disorder", *Neurosurgery*, 52(6), (Jun. 2003),1263-1276.

Geddes, L. A., et al., "The specific resistance of biological material—a compendium of data for the biomedical engineer and physiologist.", *Med Biol Eng.*, 5(3), (May 1967),271-93.

Gimsa, J. , et al., "Choosing electrodes for deep brain stimulation experiments-electrochemical considerations.", *J Neurosci Methods*, 142(2), (Mar. 30, 2005),251-65.

Goodall, E. V., et al., "Modeling study of activation and propagation delays during stimulation of peripheral nerve fibers with a tripolar cuff electrode", *IEEE Transactions on Rehabilitation Engineering*, [see also IEEE Trans. on Neural Systems and Rehabilitation], 3(3), (Sep. 1995),272-282.

Goodall, E. V., et al., "Position-selective activation of peripheral nerve fibers with a cuff electrode", *IEEE Transactions on Biomedical Engineering*, 43(8), (Aug. 1996),851-856.

Goodall, E. V., "Simulation of activation and propagation delay during tripolar neural stimulation", *Proceedings of the 15th Annual International Conference of the IEEE Engineering in Medicine and Biology Society*, (1993),1203-1204.

Grill, W. M., et al., "Deep brain stimulation creates an informational lesion of the stimulated nucleus", *Neuroreport.*, 15(7), (May 19, 2004),1137-40.

Grill, W M., et al., "Electrical properties of implant encapsulation tissue", *Ann Biomed Eng.*, vol. 22, (1994),23-33.

Grill, W M., "Modeling the effects of electric fields on nerve fibers: influence of tissue electrical properties", *IEEE Transactions on Biomedical Engineering*, 46(8), (1999),918-928.

Grill, W. M., et al., "Neural and connective tissue response to long-term implantation of multiple contact nerve cuff electrodes", *J Biomed Mater Res.*, 50(2), (May 2000),215-26.

Grill, W. M., "Neural modeling in neuromuscular and rehabilitation research", *Proceedings of the 23rd Annual International Conference of the IEEE Engineering in Medicine and Biology Society*, vol. 4, (2001),4065-4068.

Grill, W. M., et al., "Non-invasive measurement of the input-output properties of peripheral nerve stimulating electrodes", *Journal of Neuroscience Methods*, 65(1), (Mar. 1996),43-50.

Grill, W. M., et al., "Quantification of recruitment properties of multiple contact cuff electrodes", *IEEE Transactions on Rehabilitation Engineering*, [see also IEEE Trans. on Neural Systems and Rehabilitation], 4(2), (Jun. 1996),49-62.

Grill, W. M., "Spatially selective activation of peripheral nerve for neuroprosthetic applications", *Ph.D. Case Western Reserve University*, (1995),245 pages.

Grill, W. M., "Stability of the input-output properties of chronically implanted multiple contact nerve cuff stimulating electrodes", *IEEE Transactions on Rehabilitation Engineering*[see also IEEE Trans. on Neural Systems and Rehabilitation], (1998),364-373.

Grill, W. M., "Stimulus waveforms for selective neural stimulation", *IEEE Engineering in Medicine and Biology Magazine*, 14(4), (Jul.-Aug. 1995),375-385.

Grill, W. M., et al., "Temporal stability of nerve cuff electrode recruitment properties", *IEEE 17th Annual Conference Engineering in Medicine and Biology Society*, vol. 2, (1995),1089-1090.

Gross, R E., et al., "Advances in neurostimulation for movement disorders", *Neurol Res.*, 22(3), (Apr. 2000),247-258.

Haberler, C , et al., "No tissue damage by chronic deep brain stimulation in Parkinson's disease", *Ann Neurol.*, 48(3), (Sep. 2000),372-376.

Haiying, L. , et al., "Intra-operative MR-guided DBS implantation for treating PD and ET", *Proceedings of SPIE* vol. 4319, Department of Radiology & Neurosurgery, University of Minnesota, Minneapolis, MN 55455,(2001),272-276.

Hamel, W , et al., "Deep brain stimulation of the subthalamic nucleus in Parkinson's disease: evaluation of active electrode contacts", *J Neurol Neurosurg Psychiatry*, 74(8), (Aug. 2003),1036-1046.

Hardman, C. D., et al., "Comparison of the basal ganglia in rats, marmosets, macaques, baboons, and humans: volume and neuronal number for the output, internal relay, and striatal modulating nuclei", *J Comp Neurol.*, 445(3), (Apr. 8, 2002),238-55.

Hashimoto, T. , et al., "Stimulation of the subthalamic nucleus changes the firing pattern of pallidal neurons", *J Neurosci.*, 23(5), (Mar. 1, 2003),1916-23.

Haslinger, B. , et al., "Frequency-correlated decreases of motor cortex activity associated with subthalamic nucleus stimulation in Parkinson's disease.", *Neuroimage*, 28(3), (Nov. 15, 2005),598-606.

Haueisen, J , et al., "The influence of brain tissue anisotropy on human EEG and MEG", *Neuroimage*, 15(1), (Jan. 2002),159-166.

Hemm, S. , et al., "Deep brain stimulation in movement disorders: stereotactic coregistration of two-dimensional electrical field modeling and magnetic resonance imaging.", *J Neurosurg.*, 103(6):, (Dec. 2005),949-55.

Hemm, S. , et al., "Evolution of Brain Impedance in Dystonic Patients Treated by GPi Electrical Stimulation", *Neuromodulation*, 7(2), (Apr. 2004),67-75.

Hershey, T. , et al., "Cortical and subcortical blood flow effects of subthalamic nucleus stimulation in PD.", *Neurology*, 61(6), (Sep. 23, 2003),816-21.

Herzog, J. , et al., "Most effective stimulation site in subthalamic deep brain stimulation for Parkinson's disease", *Mov Disord.*, 19(9), (Sep. 2004),1050-4.

Hines, M. L., et al., "The NEURON simulation environment", *Neural Comput.*, 9(6), (Aug. 15, 1997),1179-209.

Hodaie, M , et al., "Chronic anterior thalamus stimulation for intractable epilepsy", *Epilepsia*, 43(6), (Jun. 2002),603-608.

Hoekema, R. , et al., "Multigrid solution of the potential field in modeling electrical nerve stimulation", *Comput Biomed Res.*, 31(5), (Oct. 1998),348-62.

Holsheimer, J., et al., "Chronaxie calculated from current-duration and voltage-duration data", *J Neurosci Methods*, 97(1), (Apr. 1, 2000),45-50.

Holsheimer, J., et al., "Identification of the target neuronal elements in electrical deep brain stimulation", *Eur J Neurosci.*, 12(12), (Dec. 2000),4573-7.

Jezernik, S., et al., "Neural network classification of nerve activity recorded in a mixed nerve", *Neurol Res.*, 23(5), (Jul. 2001),429-34.

Johnson, M. D., et al., "Repeated voltage biasing improves unit recordings by reducing resistive tissue impedances", *IEEE Transactions on Neural Systems and Rehabilitation Engineering*, [see also IEEE Trans. on Rehabilitation Engineering], (2005), 160-165.

Jones, D K., et al., "Optimal strategies for measuring diffusion in anisotropic systems by magnetic resonance imaging", *Magn. Reson. Med.*, 42(3), (Sep. 1999),515-525.

Kitagawa, M., et al., "Two-year follow-up of chronic stimulation of the posterior subthalamic white matter for tremor-dominant Parkinson's disease.", *Neurosurgery*, 56(2), (Feb. 2005),281-9.

Krack, P, et al., "Postoperative management of subthalamic nucleus stimulation for Parkinson's disease", *Mov. Disord.*, vol. 17(suppl 3), (2002),188-197.

Le Bihan, D, et al, "Diffusion tensor imaging: concepts and applications", *J Magn Reson Imaging*, 13(4), (Apr. 2001),534-446.

Lee, D C., et al., "Extracellular electrical stimulation of central neurons: quantitative studies", *In: Handbook of neuroprosthetic methods*, WE Finn and PG Lopresti (eds) CRC Press, (2003),95-125.

Levy, A L., et al., "An Internet-connected, patient-specific, deformable brain atlas integrated into a surgical navigation system", *J Digit Imaging*, 10(3 Suppl 1), (Aug. 1997),231-237.

Limousin, P., et al., "Electrical stimulation of the subthalamic nucleus in advanced Parkinson's disease", *N Engl J Med.*, 339(16), (Oct. 15, 1998),1105-11.

Mayberg, H. S., et al., "Deep brain stimulation for treatment-resistant depression", *Neuron*, 45(5), (Mar. 3, 2005),651-60.

McIntyre, Cameron C., et al., "Cellular effects of deep brain stimulation: model-based analysis of activation and inhibition", *J Neurophysiol*, 91(4), (Apr. 2004),1457-1469.

McIntyre, Cameron C., et al., "Electric Field and Stimulating Influence generated by Deep Brain Stimulation of the Subthalamaic Nucleus", *Clinical Neurophysiology*, 115(3), (Mar. 2004),589-595.

McIntyre, Cameron C., et al., "Electric field generated by deep brain stimulation of the subthalamic nucleus", *Biomedical Engineering Society Annual Meeting*, Nashville TN, (Oct. 2003).

McIntyre, Cameron C., et al., "Excitation of central nervous system neurons by nonuniform electric fields.", *Biophys. J.*, 76(2), (1999),878-888.

McIntyre, Cameron C., et al., "Extracellular stimulation of central neurons: influence of stimulus waveform and frequency on neuronal output", *J. Neurophysiol.*, 88(4), (Oct. 2002),1592-1604.

McIntyre, Cameron, et al., "Finite element analysis of the current-density and electric field generated by metal microelectrodes", *Ann Biomed Eng.*, 29(3), (2001),227-235.

McIntyre, C. C., et al., "How does deep brain stimulation work? Present understanding and future questions.", *J Clin Neurophysiol.*, 21(1), (Jan.-Feb. 2004),40-50.

McIntyre, C. C., et al., "Microstimulation of spinal motoneurons: a model study", *Proceedings of the 19th Annual International Conference of the IEEE Engineering in Medicine and Biology society*, vol. 5, (1997),2032-2034.

McIntyre, Cameron C., et al., "Model-based Analysis of deep brain stimulation of the thalamus", *Proceedings of the Second joint EMBS/BMES Conference*, vol. 3, Annual Fall Meeting of the Biomedical Engineering Society (Cat. No. 02CH37392) IEEE Piscataway, NJ,,(2002),2047-2048.

McIntyre, C. C., et al., "Model-based design of stimulus trains for selective microstimulation of targeted neuronal populations", *Proceedings of the 23rd Annual International Conference of the IEEE Engineering in Medicine and Biology Society*, vol. 1, (2001),806-809.

McIntyre, C. C., et al., "Model-based design of stimulus waveforms for selective microstimulation in the central nervous system", *Proceedings of the First Joint [Engineering in Medicine and Biology. 1999. 21st Annual Conf. and the 1999 Annual Fall Meeting of the Biomedical Engineering Soc.] BMES/EMBS Conference*, vol. 1, (1999),384.

McIntyre, Cameron C., et al., "Modeling the excitability of mammalian nerve fibers: influence of afterpotentials on the recovery cycle", *J Neurophysiol*, 87(2), (Feb. 2002),995-1006.

McIntyre, Cameron C., et al., "Selective microstimulation of central nervous system neurons", *Annals of biomedical engineering.*, 28(3), (Mar. 2000),219-233.

McIntyre, C. C., et al., "Sensitivity analysis of a model of mammalian neural membrane", *Biol Cybern.*, 79(1), (Jul. 1998),29-37.

McIntyre, Cameron C., et al., "Uncovering the mechanism(s) of action of deep brain stimulation: activation, inhibition, or both.", *Clin Neurophysiol*, 115(6), (Jun. 2004),1239-48.

McIntyre, Cameron C., et al., "Uncovering the mechanisms of deep brain stimulation for Parkinson's disease through functional imaging, neural recording, and neural modeling", *Crit Rev Biomed Eng.*, 30(4-6), (2002),249-281.

McNeal, D R., et al., "Analysis of a model for excitation of myelinated nerve", *IEEE Trans Biomed Eng.*, vol. 23, (1976),329-337.

Merrill, D. R., et al., "Electrical stimulation of excitable tissue: design of efficacious and safe protocols", *J Neurosci Methods*, 141(2), (Feb. 15, 2005),171-98.

Micheli-Tzanakou, E., et al., "Computational Intelligence for target assesment in Parkinson's disease", *Proceedings of SPIE* vol. 4479, Applications and Science of Neural Networks, Fuzzy Systems, and Evolutionary Computation IV,(2001),54-69.

Miocinovic, S., et al., "Computational analysis of subthalamic nucleus and lenticular fasciculus activation during therapeutic deep brain stimulation.", *J Neurophysiol.*, 96(3), (Sep. 2006),1569-80.

Miocinovic, S., et al., "Sensitivity of temporal excitation properties to the neuronal element activated by extracellular stimulation", *J Neurosci Methods*, 132(1), (Jan. 15, 2004),91-9.

Miranda, P. C., et al., "The distribution of currents induced in the brain by Magnetic Stimulation: a finite element analysis incorporating DT-MRI-derived conductivity data", *Proc. Intl. Soc. Mag. Reson. Med.* 9, (2001),1540.

Miranda, P. C., et al., "The Electric Field Induced in the Brain by Magnetic Stimulation: A 3-D Finite-Element Analysis of the Effect of Tissue Heterogeneity and Anisotropy", *IEEE Transactions on Biomedical Enginering*, 50(9), (Sep. 2003),1074-1085.

Moffitt, M A., et al., "Prediction of myelinated nerve fiber stimulation thresholds: limitations of linear models",*IEEE Transactions on Biomedical Engineering*, 51(2), (2003),229-236.

Montgomery, E. B., et al., "Mechanisms of deep brain stimulation and future technical developments.", *Neurol Res.*, 22(3), (Apr. 2000),259-66.

Moro, E, et al., "The impact on Parkinson's disease of electrical parameter settings in STN stimulation", *Neurology*, 59(5), (Sep. 10, 2002),706-703.

Moss, J., et al., "Electron microscopy of tissue adherent to explanted electrodes in dystonia and Parkinson's disease", *Brain*, 127(Pt 12), (Dec. 2004),2755-63.

Nowak, L G., et al., "Axons, but not cell bodies, are activated by electrical stimulation in cortical gray matter. I. Evidence from chronaxie measurements", *Exp. Brain Res.*, 118(4), (Feb. 1998),477-488.

Nowak, L G., et al., "Axons, but not cell bodies, are activated by electrical stimulation in cortical gray matter. II. Evidence from selective inactivation of cell bodies and axon initial segments", *Exp. Brain Res.*, 118(4), (Feb. 1998),489-500.

Nowinski, W. L., et al., "Statistical analysis of 168 bilateral subthalamic nucleus implantations by means of the probabilistic functional atlas.", *Neurosurgery*, 57(4 Suppl), (Oct. 2005),319-30.

O'Suilleabhain, P E., et al., "Tremor response to polarity, voltage, pulsewidth and frequency of thalamic stimulation", *Neurology*, 60(5), (Mar. 11, 2003),786-790.

Obeso, J. A., et al., "Deep-brain stimulation of the subthalamic nucleus or the pars interna of the globus pallidus in Parkinson's disease.", *N. Engl J Med.*, 345(13), The Deep-Brain Stimulation for Parkinson's Disease Study Group,(Sep. 27, 2001),956-63.

Patrick, S. K., et al., "Quantification of the UPDRS rigidity scale", *IEEE Transactions on Neural Systems and Rehabilitation Engineering*, [see also IEEE Trans. on Rehabilitation Engineering], 9(1), (2001),31-41.

Phillips, M. D., et al., "Parkinson disease: pattern of functional MR imaging activation during deep brain stimulation of subthalamic nucleus—initial experience", *Radiology*, 239(1), (Apr. 2006),209-16.

Pierpaoli, C, et al., "Toward a quantitative assessment of diffusion anisotropy", *Magn Reson Med.*, 36(6) (Dec. 1996),893-906.

Plaha, P., et al., "Stimulation of the caudal zona incerta is superior to stimulation of the subthalamic nucleus in improving contralateral parkinsonism.", *Brain*, 129(Pt 7), (Jul. 2006),1732-47.

Plonsey, R, et al., "Considerations of quasi-stationarity in electrophysiological systems", *Bull Math Biophys.*, 29(4), (Dec. 1967),657-664.

Ranck, J B., "Specific impedance of rabbit cerebral cortex.", *Exp. Neurol.*, vol. 7, (Feb. 1963),144-152.

Ranck, J B., et al., "The Specific impedance of the dorsal columns of the cat: an anisotropic medium", *Exp. Neurol.*, 11, (Apr. 1965),451-463.

Ranck, J B., "Which elements are excited in electrical stimulation of mammalian central nervous system: a review", *Brain Res.*, 98(3), (Nov. 21, 1975),417-440.

Rattay, F., et al., "A model of the electrically excited human cochlear neuron. I. Contribution of neural substructures to the generation and propagation of spikes", *Hear Res.*, 153(1-2), (Mar. 2001),43-63.

Rattay, F., "A model of the electrically excited human cochlear neuron. II. Influence of the three-dimensional cochlear structure on neural excitability", *Hear Res.*, 153(1-2), (Mar. 2001),64-79.

Rattay, F, "Analysis of models for external stimulation of axons", *IEEE Trans. Biomed. Eng.*, vol. 33, (1986),974-977.

Rattay, F., "Analysis of the electrical excitation of CNS neurons", *IEEE Transactions on Biomedical Engineering*, 45(6), (Jun. 1998),766-772.

Rattay, F., "Arrival at Functional Electrostimulation by modelling of fiber excitation", *Proceedings of the Ninth annual Conference of the IEEE Engineering in Medicine and Biology Society*, (1987),1459-1460.

Rattay, F., "The influence of intrinsic noise can preserve the temporal fine structure of speech signals in models of electrically stimulated human cochlear neurones", *Journal of Physiology*, Scientific Meeting of the Physiological Society, London, England, UK Apr. 19-21, 1999,(Jul. 1999),170P.

Rizzone, M, et al., "Deep brain stimulation of the subthalamic nucleus in Parkinson's disease: effects of variation in stimulation parameters", *J. Neurol. Neurosurg. Psychiatry.*, 71(2), (Aug. 2001),215-219.

Rose, T. L., et al., "Electrical stimulation with Pt electrodes. VIII. Electrochemically safe charge injection limits with 0.2 ms pulses [neuronal application]", *IEEE Transactions on Biomedical Engineering*, 37(11), (Nov. 1990),1118-1120.

Rubinstein, J. T., et al., "Signal coding in cochlear implants: exploiting stochastic effects of electrical stimulation", *Ann Otol Rhinol Laryngol Suppl.*, 191, (Sep. 2003),14-9.

Saint-Cyr, J A., et al., "Localization of clinically effective stimulating electrodes in the human subthalamic nucleus on magnetic resonance imaging", *J. Neurosurg.*, 87(5), (Nov. 2002),1152-1166.

Sances, A, et al., "In Electroanesthesia: Biomedical and Biophysical Studies", A Sances and SJ Larson, Eds., Academic Press, NY, (1975),114-124.

Schwan, H. P., et al., "The conductivity of living tissues.", *Ann N Y Acad Sci.*, 65(6), (Aug. 1957),1007-13.

Sotiropoulos, P. N., et al., "A biophysical model of deep brain stimulation of the subthalamic nucleus", *Society for Neuroscience Meeting*, 1011.5,(2004).

St. Jean, P, et al., "Automated atlas integration and interactive three-dimensional visualization tools for planning and guidance in functional neurosurgery", *IEEE Transactions on Medical Imaging*, 17(5), (1998),672-680.

Starr, P A., et al., "Implantation of deep brain stimulators into the subthalamic nucleus: technical approach and magnetic resonance imaging-verified lead locations", *J. Neurosurg.*, 97(2), (Aug. 2002),370-387.

Sterio, D, et al., "Neurophysiological refinement of subthalamic nucleus targeting", *Neurosurgery*, 50(1), (Jan. 2002),58-67.

Struijk, J. J., et al., "Excitation of dorsal root fibers in spinal cord stimulation: a theoretical study", *IEEE Transactions on Biomedical Engineering*, 40(7), (Jul. 1993),632-639.

Struijk, J J., et al., "Recruitment of dorsal column fibers in spinal cord stimulation: influence of collateral branching", *IEEE Transactions on Biomedical Engineering*, 39(9), (Sep. 1992),903-912.

Tamma, F, et al., "Anatomo-clinical correlation of intraoperative stimulation-induced side-effects during HF-DBS of the subthalamic nucleus", *Neurol Sci.*, vol. 23 (Supp. 2), (2002),109-110.

Tarler, M., et al., "Comparison between monopolar and tripolar configurations in chronically implanted nerve cuff electrodes", *IEEE 17th Annual Conference Engineering in Medicine and Biology Society*, vol. 2, (1995),1093-1094.

Taylor, R. S., et al., "Spinal cord stimulation for chronic back and leg pain and failed back surgery syndrome: a systematic review and analysis of prognostic factors", *Spine*, 30(1) (Jan. 1, 2005),152-60.

Testerman, Roy L., "Coritical response to callosal stimulation: A model for determining safe and efficient stimulus parameters", *Annals of Biomedical Engineering*, 6(4), (1978),438-452.

Trost, M., et al., "Network modulation by the subthalamic nucleus in the treatment of Parkinson's disease", *Neuroimage*, 31(1), (May 15, 2006),301-7.

Tuch, D S., et al., "Conductivity mapping of biological tissue using diffusion MRI.", *Ann N Y Acad Sci.*, 888, (Oct. 30, 1999),314-316.

Tuch, D S., et al., "Conductivity tensor mapping of the human brain using diffusion tensor MRI", *Proc Natl Acad Sci U S A.*, 98(20), (Sep. 25, 2001),11697-11701.

Tyler, R. S., et al., "Update on bilateral cochlear implantation", *Curr Opin Otolaryngol Head Neck Surg.*, 11(5), (Oct. 2003),388-93.

Veraart, C., et al., "Selective control of muscle activation with a multipolar nerve cuff electrode", *IEEE Transactions on Biomedical Engineering*, 40(7), (Jul. 1993),640-653.

Vercueil, L, et al., "Deep brain stimulation in the treatment of severe dystonia", *J. Neurol.*, 248(8), (Aug. 2001),695-700.

Vidailhet, M., et al., "Bilateral deep-brain stimulation of the globus pallidus in primary generalized dystonia", *N Engl J Med.*, 352(5), (Feb. 3, 2005),459-67.

Viola, P., et al., "Alignment by maximization of mutual information", *International Journal of Computer Vision*, 24(2), (1997),137-154.

Vitek, J L., "Mechanisms of deep brain stimulation: excitation or inhibition", *Mov. Disord.*, vol. 17 (Suppl. 3), (2002),69-72.

Voges, J, et al., "Bilateral high-frequency stimulation in the subthalamic nucleus for the treatment of Parkinson disease: correlation of therapeutic effect with anatomical electrode position", *J. Neurosurg.*, 96(2), (Feb. 2002),269-279.

Volkmann, J., et al., "Basic algorithms for the programming of deep brain stimulation in Parkinson's disease", *Mov Disord.*, 21 Suppl 14, (Jun. 2006),S284-9.

Volkmann, J, et al., "Introduction to the programming of deep brain stimulators", *Mov. Disord.*, vol. 17 (Suppl 3), (2002),181-187.

Wakana, S, et al., "Fiber tract-based atlas of human white matter anatomy", *Radiology.* 230(1), (Jan. 2004),77-87.

Walter, B. L., et al., "Surgical treatment for Parkinson's disease", *Lancet Neurol.*, 3(12), (Dec. 2004),719-28.

Warman, E N., et al., "Modeling the effects of electric fields on nerve fibers: Determination of excitation thresholds", *IEEE Transactions on Biomedical Engineering*, 39(12), (1992),1244-1254.

Wei, X. F., et al., "Current density distributions, field distributions and impedance analysis of segmented deep brain stimulation electrodes", *J Neural Eng.*, 2(4), (Dec. 2005),139-47.

Wu, Y R., et al., "Does Stimulation of the GPi control dyskinesia by activating inhibitory axons?", *Mov. Disord.*, vol. 16, (2001),208-216.

Yelnik, J., et al., "Localization of stimulating electrodes in patients with Parkinson disease by using a three-dimensional atlas-magnetic resonance imaging coregistration method", *J Neurosurg.*, 99(1), (Jul. 2003),89-99.

Yianni, John, et al., "Globus pallidus internus deep brain stimulation for dystonic conditions: a prospective audit", *Mov. Disord.*, vol. 18, (2003),436-442.

Zonenshayn, M., et al., "Comparison of anatomic and neurophysiological methods for subthalamic nucleus targeting", *Neurosurgery*, 47(2), (Aug. 2000),282-292.

Zonenshayn, M., et al., "Location of the active contact within the subthalamic nucleus (STN) in the treatment of idiopathic Parkinson's disease.", *Surg Neurol.*, 62(3), (Sep. 2004),216-25.

SYSTEM AND METHOD FOR OBTAINING A VOLUME OF INFLUENCE BASED ON NON-UNIFORM TISSUE CONDUCTIVITY DATA

CROSS-REFERENCE TO RELATED APPLICATION

This application is a divisional of U.S. patent application Ser. No. 10/885,982, filed Jul. 7, 2004, which issued on Mar. 18, 2008 as U.S. Pat. No. 7,346,382, and which is hereby incorporated by reference.

TECHNICAL FIELD

This patent application pertains generally to neurosurgery and more particularly, but not by way of limitation, to brain stimulation models, systems, devices, and methods.

BACKGROUND

High frequency deep brain stimulation (DBS), such as of the thalamus or basal ganglia, represents a clinical technique for the treatment of disorders such as essential tremor and Parkinson's disease (PD). Pilot studies have also begun to examine the utility of DBS for treating dystonia, epilepsy, and obsessive-compulsive disorder. However, understanding of the therapeutic mechanisms of action remains elusive. It is also unclear what stimulation parameters, electrode geometries, or electrode locations are better suited for existing or future uses of DBS.

A DBS procedure typically involves first obtaining preoperative images of the patient's brain, such as by using a computed tomography (CT) scanner device, a magnetic resonance imaging (MRI) device, or any other imaging modality. This sometimes involves first affixing to the patient's skull spherical or other fiducial markers that are visible on the images produced by the imaging modality. The fiducial markers help register the preoperative images to the actual physical position of the patient in the operating room during the later surgical procedure.

After the preoperative images are acquired by the imaging modality, they are then loaded onto an image-guided surgical (IGS) workstation, such as the StealthStation® from the Surgical Navigation Technologies, Inc. (SNT) subsidiary of Medtronic, Inc., for example. Using the preoperative images being displayed on the IGS workstation, the neurosurgeon can select a target region within the brain, an entry point on the patient's skull, and a desired trajectory between the entry point and the target region. The entry point and trajectory are typically carefully selected to avoid intersecting or otherwise damaging certain nearby critical brain structures.

In the operating room, the patient is immobilized and the patient's actual physical position is registered to the preoperative images displayed on the IGS workstation, such as by using a remotely detectable IGS wand. In one example, the physician marks the entry point on the patient's skull, drills a burr hole at that location, and affixes a trajectory guide device about the burr hole. The trajectory guide device includes a bore that can be aimed using the IGS wand to obtain the desired trajectory to the target region. After aiming, the trajectory guide is locked to preserve the aimed trajectory toward the target region.

After the aimed trajectory has been locked in using the trajectory guide, a microdrive introducer is used to insert the surgical instrument along the trajectory toward the target region of the brain. The surgical instrument may include, among other things, a recording electrode leadwire, for recording intrinsic electrical brain signals, a stimulation electrode leadwire, for providing electrical energy to the target region of the brain, or associated auxiliary guide catheters for steering a primary instrument toward target region of the brain. The recording electrode leadwire is typically used first to confirm, by interpreting the intrinsic electrical brain signals, that a particular location along the trajectory is indeed the desired target region of the brain. The stimulation electrode leadwire, which typically includes multiple closely-spaced electrically independent stimulation electrode contacts, is then introduced to deliver the therapeutic DBS stimulation to the target region of the brain. The stimulation electrode leadwire is then immobilized, such as by using an instrument immobilization device located at the burr hole entry in the patient's skull. The actual DBS therapy is often not initiated until a time period of about two-weeks to one month has elapsed. This is due primarily to the acute reaction of the brain tissue to the introduced DBS stimulation electrode leadwire (e.g., the formation of adjacent scar tissue), and stabilization of the patient's disease symptoms. At that time, a particular one of the stimulation electrode contacts is then selected for delivering the therapeutic DBS stimulation, and other DBS parameters are adjusted to achieve an acceptable level of therapeutic benefit. However, these parameter selections are typically currently achieved via arbitrary trial-and-error, without visual aids of the electrode location in the tissue medium or computational models of the volume of tissue influenced by the stimulation.

The subthalamic nucleus (STN) represents the most common target for DBS technology. Clinically effective STN DBS for PD has typically used electrode contacts in the anterior-dorsal STN. However, STN DBS exhibits a low threshold for certain undesirable side effects, such as tetanic muscle contraction, speech disturbance and ocular deviation. Highly anisotropic fiber tracks are located about the STN. Such nerve tracks exhibit high electrical conductivity in a particular direction. Activation of these tracks has been implicated in many of the DBS side effects. However, there exists a limited understanding of the neural response to DBS. The three-dimensional (3D) tissue medium near the DBS electrode typically includes both inhomogeneous and anisotropic characteristics. Such complexity makes it difficult to predict the particular volume of tissue influenced by DBS.

A treating physician typically would like to tailor the DBS parameters (such as which one of the stimulating electrodes to use, the stimulation pulse amplitude, the stimulation pulse width, or the stimulation frequency) for a particular patient to improve the effectiveness of the DBS therapy. This is a complex problem because there are several different DBS parameters than can be varied. Because selecting a particular DBS electrode contact and parameter combination setting is typically a trial-and-error process, it is difficult and time-consuming and, therefore, expensive. Moreover, it may not necessarily result in the best possible therapy or in avoiding the above-mentioned undesirable side effects. Therefore, there is a need to provide help to speed or otherwise improve this DBS parameter selection process or to otherwise enhance DBS techniques.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1A:
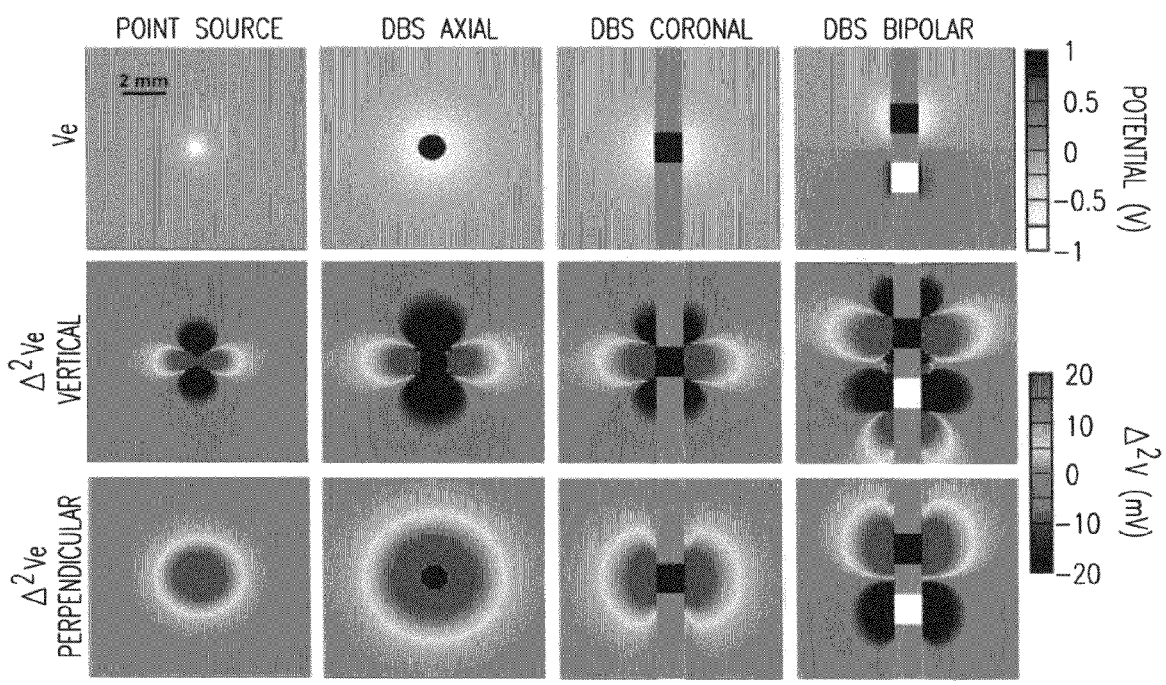
FIG. 1A is a series of color panels illustrating examples of modeled potential distributions and second differences of potential distributions for various electrode configurations.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

1. Modeling Techniques

A. Introduction

One fundamental step toward understanding the neural response to DBS is characterizing the electric field generated by a stimulating electrode. The electric field is dependent on the shape of the electrode and the electrical conductivity of the tissue medium. DBS electrodes are three-dimensional structures and the tissue conductivity of the central nervous system (CNS) is both inhomogeneous (dependent on location) and anisotropic (dependent on direction). The tissue inhomogeneity and anisotropy surrounding the DBS electrode can alter the shape of the electric field and the subsequent neural response to stimulation. Therefore, in one example, we employed diffusion tensor imaging (DTI) to estimate the electrical conductivity tensor of the tissue medium surrounding one or more DBS electrodes. We incorporated the tissue conductivity data into a finite element model (FEM) tailored to accurately represent the structure of the particular clinical DBS electrode and surrounding tissue medium. We then used these models to predict the volume of tissue likely to be affected by typical stimulation parameters (e.g., stimulation pulse amplitude of between about 1 and 3 Volts, a stimulation pulsewidth of about 0.1 ms, and a stimulation frequency of about 150 Hz). We refer to this volume of tissue likely to be affected as the "volume of influence" (VOI) or "volume of activation" (VOA).

B. Exemplary Methods

We developed, among other things, three-dimensional finite element models (FEMs) of the Medtronic 3387-89 DBS lead (Medtronic, Inc., Minneapolis, Minn.). We examined at least two representations of the nearby tissue electrical properties. In one example, the finite element model used a constant homogenous isotropic tissue conductivity of about 0.3 S/m. In another example, the finite element model explicitly represented tissue anisotropy with conductivity tensors (σ) derived from diffusion tensor magnetic resonance images. Both examples of finite element models used an about 0.2 mm thick sheath of encapsulation tissue (modeled with a conductivity of about 0.15 S/m) about the DBS electrode leadwire shaft. In one example, the FEM was implemented using 231, 404 elements in a commercially available software package such as FEMLAB 2.3 (COMSOL Inc., Burlington, Mass.). In one example, a 100×100×100 mm³ cube about the electrode contact was used as a FEM model boundary, which was set to a boundary condition of 0 V. In this example of the FEM model, the electrode contact was set to a boundary condition of the DBS stimulus voltage. The potential distribution ($V_e$) generated in the tissue medium was calculated from the Laplace equation:

$$\nabla \cdot \sigma \nabla V_e = 0, \qquad \text{(Eq. 1)}$$

using a Good Broyden iterative solver and algebraic multigrid preconditioner. Doubling the density of the FEM mesh or doubling the distance of the boundary from the electrode (i.e., quadrupling the size of the 100×100×100 mm³ tissue box) yielded a potential distribution $V_e$ that differed only by less than 2% when compared to the default model.

Diffusion tensor imaging (DTI) characterizes the diffusional behavior of water in tissue on a voxel-by-voxel basis in terms of a matrix quantity from which the diffusion coefficient can be obtained corresponding to any direction in space.

The electrical conductivity tensor (σ) of a tissue medium is obtainable from the corresponding diffusion tensor (D). The hypothesized relationship between electrical conductivity and water diffusion in tissue is prompted by the observation that in a structured medium the two processes are related through mutual respect for the boundary conditions imposed by the tissue geometry. In our example, the conductivity tensor σ was directly solved for at each voxel using a linear transform of D:

$$\sigma = (\sigma_e/d_e)D, \quad (Eq. 2)$$

where $\sigma_e$ is the effective extracellular conductivity and $d_e$ is the effective extracellular diffusivity. Our example used a ratio of $((\sigma_e/d_e)=0.736$ (S–s)/mm$^2$) as determined from published experimental and empirical data.

In one example, the DTI data was acquired using a 1.5 T Philips Gyroscan NT using a single-shot echo-planar imaging (EPI) sequence with the SENSE parallel imaging scheme (SENSitivity Encoding, reduction factor R=2.5). In this example, the imaging matrix was 96×96 with a field of view of 240×240 mm, which was zero-filled to 256×256. In this example, axial slices of 2.5 mm thickness were acquired parallel to the anterior-posterior commissure line. In this example, the diffusion weighting was encoded along 30 independent orientations and the b-value was 700 s/mm$^2$. In this example, the dorsal STN was located in axial slices using stereotactic coordinates and co-registration with the Schlatlenbrand and Bailey [1959] brain atlas. We extracted the DTI data from the 10×10 mm region that surrounded our electrode location in the STN (in this example, the electrode was located 2 mm ventral, 10 mm lateral, and 1 mm posterior to the mid-commissural point). We then transformed the diffusion tensors to conductivity tensors, as discussed above. We then incorporated the conductivity tensors into co-registered subdomains in the FEM. Then, using the FEM, we solved for the potential distribution generated in the tissue medium by DBS, as discussed above.

C. Exemplary Results

Using the exemplary methods discussed above, we compared the electric field of a theoretical point source, a DBS electrode in an isotropic medium, and a DBS electrode in an anisotropic medium representative of the STN and surrounding tissue structures.

FIG. 1A shows examples of the potential distribution ($V_e$) generated in the tissue medium for each of these models (first row of FIG. 1A) as well as the second difference of the potential ($\Delta^2 V_e$) evaluated at 0.5 mm increments along different directions (i.e., $\Delta^2 V_e = V_e[n+0.5\text{ mm}] + V_e[n-0.5\text{ mm}] - 2*V_e[n]$). The $\Delta^2 V_e$ along individual neuronal processes induces transmembrane currents. The induced transmembrane currents result in direct polarization of the neuron by the applied electric field. The second difference $\Delta^2 V_e$ has both positive and negative components along any given direction. This results in regions of both depolarization (positive $\Delta^2 V_e$) and hyperpolarization (negative $\Delta^2 V_e$) in neurons near the electrode, as illustrated in FIG. 1A.

FIG. 1A illustrates examples of a potential distribution ($V_e$) and its second difference ($\Delta^2 V_e$). FIG. 1A compares (for an isotropic tissue medium) a monopolar point source (−1 mA stimulation current; illustrated in the left column of FIG. 1A), a monopolar DBS leadwire electrode (−1 V stimulation voltage, illustrated in the middle two columns of FIG. 1A), and a bipolar DBS leadwire with two electrode contacts (+/−1 V stimulation voltages, respectively, illustrated in the right column of FIG. 1A).

The top row of FIG. 1A shows $V_e$ over a 10×10 mm$^2$ area, with lighter color tones indicating a more negative potential, and darker color tones indicating a more positive potential.

The middle row of FIG. 1A shows $\Delta^2 V_e$ evaluated along a vertical direction relative to the displayed plane in the top row of FIG. 1A. The bottom row of FIG. 1A shows $\Delta^2 V_e$ evaluated along a direction perpendicular to the displayed plane in the top row of FIG. 1A. Positive $\Delta^2 V_e$ is representative of a depolarizing influence, which are indicated by redder color tones. Negative $\Delta^2 V_e$ is representative of a hyperpolarizing influence, which are indicated by bluer color tones. $\Delta^2 V_e$ values >20 mV and <−20 mV are clipped to provide better resolution of the values of interest.

For the point source, $\Delta^2 V_e$ vertical (i.e., the left middle picture of FIG. 1A) has hyperpolarized top and bottom lobes and depolarized left and right lobes. For the axial view of the monopolar DBS source, $\Delta^2 V_e$ vertical (i.e., the second from left picture in the middle row of FIG. 1A) has hyperpolarized top and bottom lobes and depolarized left and right lobes. For the coronal view of the monopolar DBS source, $\Delta^2 V_e$ vertical (i.e., the second from right picture in the middle row of FIG. 1A) has hyperpolarized top and bottom lobes and depolarized left and right lobes. For the bipolar DBS source, $\Delta^2 V_e$ vertical (i.e., the right-most picture in the middle row of FIG. 1A) exhibits, for the upper (positive) electrode, hyperpolarized top and bottom lobes and depolarized left and right lobes. The bottom lobe is smaller than the top lobe. In this same picture, the lower (negative) electrode exhibits depolarized top and bottom lobes and hyperpolarized left and right lobes. The top lobe is smaller than the bottom lobe. The $\Delta^2 V_e$ perpendicular illustrated by the bottom row of FIG. 1A illustrates depolarization, except for the lower (negative) electrode of the DBS bipolar source in the right-most picture, which exhibits hyperpolarized lobes.

Figure 1B:
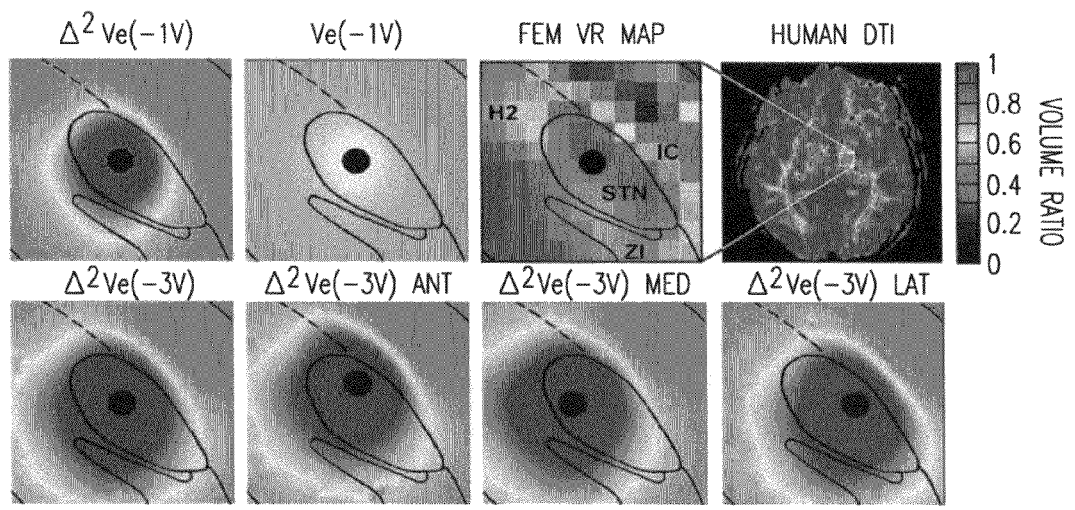
FIG. 1B is a series of color panels illustrating examples of a human diffusion tensor image, a volume ratio map representing a portion thereof, and a modeled potential distribution and second differences of potential distributions for various electrode positions.

FIG. 1B illustrates an example of a monopolar DBS source in an anisotropic medium that is representative of the STN and surrounding tissue structures. The right two panels of the top row of FIG. 1B show the volume ratio (VR), that is, $\lambda_1 \lambda_2 \lambda_3/[(\lambda_1+\lambda_2+\lambda_3)/3]^3$. The VR is a scalar that quantifies the degree of anisotropy in each voxel using the eigenvalues ($\lambda_1, \lambda_2, \lambda_3$) of the diffusion tensor, such as for the entire axial slice of the patient's brain (illustrated in the far right panel of the top row of FIG. 1B) and for the 10×10 region about the STN that was used in the FEM (illustrated in the middle right panel of the top row of FIG. 1B). For this 10×10 region, dark overlaid lines indicate, for reference purposes, the representative anatomical location of the STN as obtained using the Schlatlenbrand and Bailey brain atlas or the like.

In the example of FIG. 1B, the middle left panel of the top row shows $V_e$ generated from a −1 V stimulus from a monopolar DBS source. The far left panel in the top row of FIG. 1B shows $\Delta^2 V_e$ evaluated along the direction perpendicular to the displayed plane in the middle left panel of the top row of FIG. 1B for a −1 V stimulus. The bottom row of FIG. 1B shows $\Delta^2 V_e$ for a −3 V stimulus with the electrode located in the anterior-dorsal STN (far left panel of the bottom row of FIG. 1B), located 1 mm anterior (middle left panel of the bottom row of FIG. 1B), 1 mm medial (middle right panel of the bottom row of FIG. 1B), and 1 mm lateral (far right panel of the bottom row of FIG. 1B).

Because $\Delta^2 V_e$ represents the effective volume of activation of nearby tissue, this model can be used to adjust the electrode location or stimulation parameters to obtain a desired volume of activation for the DBS stimulation, such as to activate substantially the entire STN, as illustrated by the location and the −3V stimulation in the bottom far right panel of FIG. 1B, for example.

During extracellular stimulation of the CNS, axonal elements typically represent the most excitable components of neurons near the electrode. Evaluation of $\Delta^2 V_e$ can provide qualitative predictions on the likelihood of neural activation by an extracellular source. Therefore, to provide a quantitative reference to the $\Delta^2 V_e$ data in FIGS. 1A and 1B, we used the 5.7 μm diameter myelinated axon model from Cameron C. McIntyre et al., "Modeling the Excitability of Mammalian Nerve Fibers: Influence of Afterpotentials on the Recovery Cycle," J. Neurophysiology, Vol. 87, February 2002, pp. 995-1006, which is incorporated herein by reference in its entirety, to draw correlations between axonal threshold and $\Delta^2 V_e$. (Alternatively, instead of using an axon model, a more detailed neuronal model could be used, such as described in Cameron C. McIntyre et al., "Cellular Effects of Deep Brain Stimulation: Model-Based Analysis of Activation and Inhibition," J. Neurophysiology 91: 1457-1469 (2004), which is incorporated by reference herein in its entirety). A Δx of 0.5 mm was used in evaluating $\Delta^2 V_e$ as this distance represents the internodal spacing of the 5.7 μm fiber axon model. Fifty modeled axons oriented parallel to the electrode shaft were randomly positioned in the tissue medium surrounding the electrode. Then, the $\Delta^2 V_e$ was calculated for threshold stimulation of the modeled axons. The results are illustrated in FIG. 2.

Figure 2:
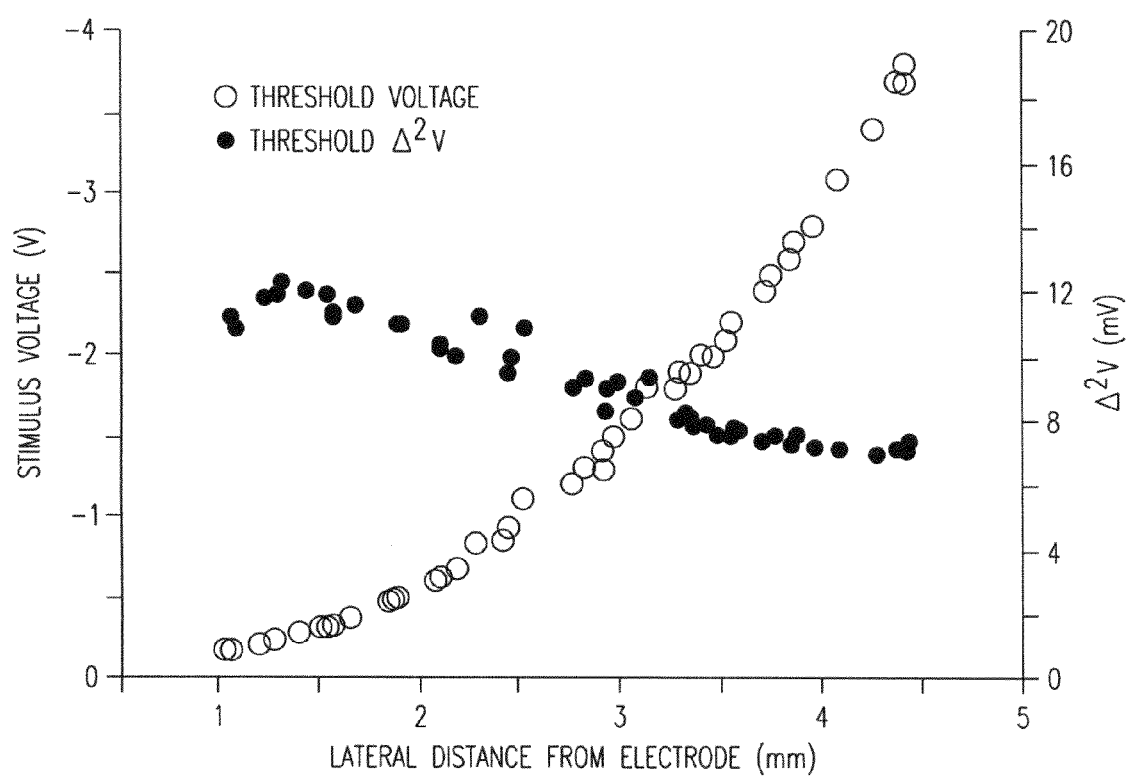
FIG. 2 is a graph illustrating an example of lateral distance from an electrode plotted on a x-axis, and axon stimulating threshold voltage plotted on a first y-axis, and the axon stimulating second difference threshold voltage plotted on a second y-axis.

FIG. 2 is a graph that illustrates generally one example of a current distance relationship of large diameter axons during DBS. In the example of FIG. 2, a threshold stimulus amplitude was calculated for fifty 5.7 μm diameter myelinated axons to follow a 150 Hz train of 0.1 ms duration DBS stimulation pulses as a function of their distance from the DBS electrode. In this example, the axons were randomly positioned in the tissue medium and oriented parallel to the electrode shaft. The second difference of the potential distribution (Δx=0.5 mm) at threshold was calculated for each axon along its path length and at the point in axial plane that slices through the center of the stimulating contact (e.g., [$\Delta^2 V_e$ perpendicular, DBS axial] of FIG. 1A).

This analysis revealed that for a 150 Hz train of cathodic stimuli 0.1 ms in duration a $\Delta^2 V_e > 12$ mV always generated propagating action potentials at the stimulus frequency. When the axon was further than 3 mm from the electrode, a $\Delta^2 V_e > 8$ mV was enough for activation. Also, in this example, the axon model never blocked firing during −3 V; 0.1 ms; 150 Hz stimulation for any of the positions examined.

Returning to FIG. 1A, we evaluated $\Delta^2 V_e$ along several directions relative to the electrode contact. The respective red and blue of $\Delta^2 V_e$ vertical (shown in middle row in FIG. 1A) represent regions of respective depolarization and hyperpolarization that would be generated in neural elements running vertically in the displayed plane (i.e., up or down the page). $\Delta^2 V_e$ perpendicular (shown in the bottom row of FIG. 1A) represents regions of depolarization and hyperpolarization that would be generated in neural elements running perpendicular to the displayed plane (i.e., into or out of the page). $\Delta^2 V_e$ typically results in both positive and negative regions in the tissue medium. However, exemplary results from $\Delta^2 V_e$ perpendicular (shown in the bottom row of FIG. 1A) only show depolarizing effects. In these examples, hyperpolarizing effects still exist in the tissue medium, but because of the 3D nature of the stimulation they are not within the field of view that is shown.

In FIG. 1A, a coupled comparison of ($\Delta^2 V_e$ vertical, DBS axial) and ($\Delta^2 V_e$ perpendicular, DBS coronal) or ($\Delta^2 V_e$ perpendicular, DBS axial) and ($\Delta^2 V_e$ vertical, DBS coronal) show orthogonal planes through the center of the electrode contact where $\Delta^2 V_e$ has been evaluated along the same direction relative to the electrode and can give a sense of the 3D stimulation effects. In this example, the model results show that monopolar −1 V stimuli activated large diameter axons within about a 2.5 mm radius of the electrode contact, as illustrated by FIG. 1A and FIG. 2. Bipolar stimulation generated a more complex pattern of depolarization and hyperpolarization. However, bipolar stimulation did not dramatically alter the volume of tissue above-threshold for activating large diameter axons, as shown in FIG. 1A.

FIG. 1B illustrates the incorporation of tissue electrical properties representative of the STN and surrounding structures, as discussed above. As shown in FIG. 1B, this resulted in distortion of $V_e$ and $\Delta^2 V_e$ generated by DBS as compared to the isotropic case of FIG. 1A. More particularly, the strong dorsal-ventral anisotropy of the internal capsule (IC) limited stimulation anterior and lateral to the electrode. The moderate anterior-posterior anisotropy of the region around zona incerta (ZI) extended stimulation posterior to the electrode. Increasing the stimulus amplitude to −3 V resulted in a volume of activation (represented by the second difference $\Delta^2 V_e$) that was more dependent on the tissue anisotropy and spread outside the borders of the STN. In addition, medial-lateral and/or anterior-posterior variation in the electrode location within STN directly altered the shape and volume of activation, as shown in FIG. 1B. An electrode positioned near the anterior and/or lateral borders of the STN exhibited strong activation of IC, while an electrode located in the medial STN resulted in the largest overall volume of activation and resulted in only limited activation of the IC. These results show that a minor change (e.g., on the order of 1 mm) in the electrode location within the dorsal STN can have a substantial effect on the neural response to DBS.

D. Discussion of Exemplary Results

DBS represents an effective clinical therapy for movement disorders. However, the existing limited understanding of the effects of stimulation on the underlying neural tissue hinders future advancement of this technology. The electric field generated by one or more DBS electrodes, using therapeutic DBS stimulation parameters, can directly activate a large volume of tissue, as illustrated by FIGS. 1A, 1B, and 2. One example of our model provided results that show that the stimulating effect of the electric field can spread outside the borders of the dorsal STN and can result in activation of axonal elements in the zona incerta (ZI), fields of Forel (H2), and internal capsule (IC), as shown in FIG. 1B. These model predictions agree with clinical data indicating that stimulation amplitudes in the range of −3 V are often capable of inducing side effects that are associated with activation of the corticospinal and corticobulbar tracts of the IC. Our models suggest that the low threshold side effects of IC stimulation can be avoided with electrode locations slightly (e.g., about 1 mm) medial or posterior to the clinical target of the anterior-dorsal STN. However, given the intrinsic error in the DBS implantation procedure, it is typically not presently possible to position the electrode with sub-millimeter accuracy relative to the patient specific neuroanatomy. Also, the clinical effect of the spread of stimulation outside the borders of STN to ZI and H2 is unclear. Although the present model results act as a guide to the spread of stimulation, they may not alter present DBS implantation procedures. However, the present models may alter future DBS implantation procedures or present or future DBS parameter adjustments.

The present model provides quantitative results on the effects of DBS that would be difficult to achieve experimentally. Like most models, however, they involved some simplifying approximations worth noting. First, we used electrostatic analysis and the resolution of our diffusion tensor based tissue conductivities was on the order of 1 mm. In general, however CNS tissue typically has a small reactive component that results in slight increases in conductivity at higher frequencies. Also, micro-inhomogeneities exist on scales smaller than the 1 mm. However, a reactive component or higher resolution diffusion tensor based conductivity could be used with the present model techniques, if desired.

Second, neural activation that results from applied fields could be more accurately predicted by directly coupling the electric field data to multi-compartment cable models of individual neurons. The present model techniques, however, provide easier estimation of the volume of tissue supra-threshold, and our estimation is derived directly from the field data. By evaluating $\Delta^2V_e$ in a plane containing the electrode contact, one can conceptualize the spatial characteristics of the depolarizing influence of the field, as illustrated in FIGS. 1A and 1B. By explicitly calculating the $\Delta^2V_e$ needed to activate large diameter axons (8 mV for large electrode-to-axon distances), our models provide a worst-case scenario to address the spread of stimulation, as illustrated in FIG. 2, so as to avoid unwanted side effects. This simplified estimation of the spatial extent of DBS on large diameter axons typically has an associated error of several hundred micrometers. However, given the large volume tissue affected by DBS, this error is relatively small, especially for high stimulus amplitudes, as illustrated in FIG. 2. Nonetheless, our model of STN DBS represents a significant improvement over any model that attempts to characterize the spatial extent of stimulation using empirical observations that ignore the tissue electrical properties (e.g., inhomogeneity and anisotropy) and electrode geometry.

Extracellular stimulation typically generates a complex electric field in the tissue medium that is applied to the underlying neural processes as a distribution of extracellular potentials. As derived from the cable equation, the second derivative of the extracellular potentials along each process will typically produce both transmembrane and axial currents that will be distributed throughout the neuron. In turn, each neuron exposed to the applied field will typically experience both inward and outward transmembrane currents and regions of depolarization and hyperpolarization. These theoretical predictions have been verified in numerous experimental preparations demonstrating the differences between anodic, cathodic, and bipolar stimulation on the ability to both activate and block neural activity with extracellular stimulation.

Analysis of the effects of DBS is complicated by our limited understanding of the response of neurons near the electrode to the applied fields. Addressing the effects of high frequency DBS presents investigators with a paradox of how stimulation (traditionally thought to activate neurons) can result in similar therapeutic outcomes as lesioning target structures in the thalamus or basal ganglia. There exist two general philosophies on the effects of DBS: 1) DBS is believed to generate a functional ablation by suppressing or inhibiting the structure being stimulated or 2) DBS is believed to result in activation patterns in the stimulated network that override pathological network activity. Our model results support the latter theory by showing with detailed models and therapeutically effective stimulation parameters that axonal elements are activated over a large volume of tissue surrounding the electrode.

Experimental investigation on the effects of STN DBS has implicated activation of large diameter fiber tracks with therapeutic stimulation parameters. Predictions of the volume of tissue affected by DBS, using current-density calculations, have suggested that axonal elements would be activated over a 2.5 mm radius of the electrode contact using a −3 V stimulus. However, current-density is not directly related to the neural response to stimulation, and typically has a non-uniform distribution on DBS electrode contacts. A scaled version of the derivative of the current-density, $\Delta^2V_e$, represents a value that more accurately quantifies the stimulating influence of the electric field. Using $\Delta^2V_e$ in combination with tissue electrical properties derived from DTI we predict that −3V STN DBS can activate axonal elements in STN, ZI, H2, and IC spreading as far as 4 mm from the electrode contact, as illustrated in FIG. 1B. Furthermore, the anisotropic tissue properties near the STN as well as the electrode location within the STN directly affect the size and shape of the activated volume of tissue.

2. Examples of Using a Model

Figure 3:
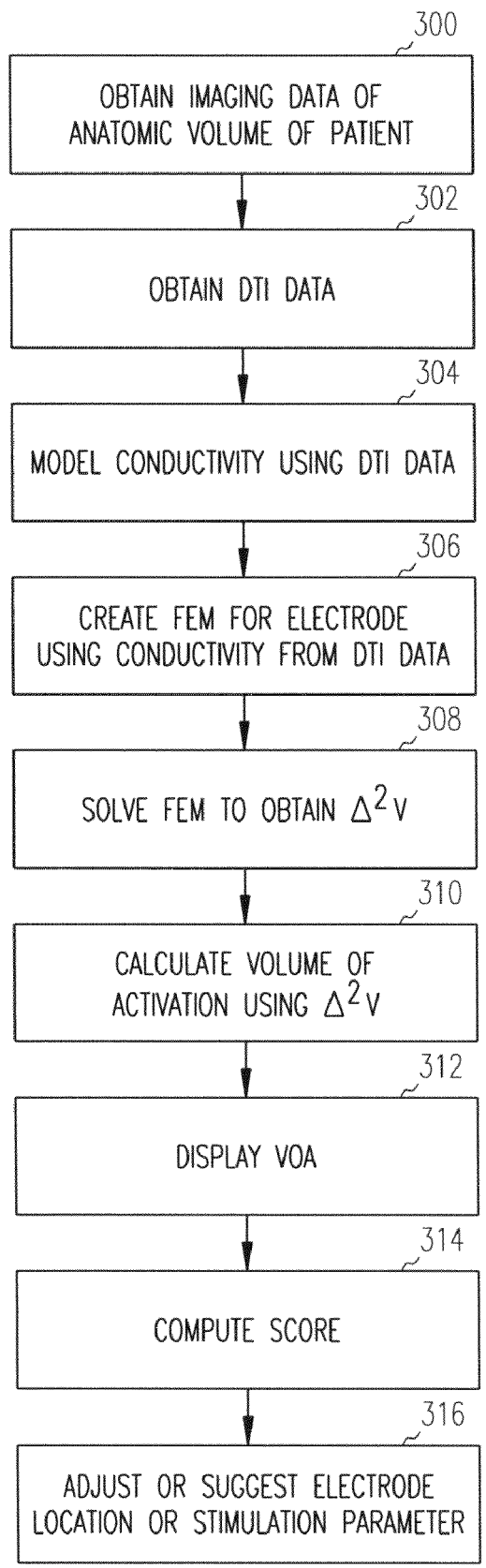
FIG. 3 is a flow chart illustrating generally one example of a method of using a model to calculate a volume of activation, as discussed above.

FIG. 3 is a flow chart illustrating generally one example of a method of using a model to calculate a volume of activation, as discussed above. Portions of the method may be embodied in any machine-accessible medium carrying instructions for executing acts included in the method. Such a method applies to deep brain stimulation (DBS) or any other electrical tissue stimulation. At 300, imaging data of an anatomic volume of a patient is obtained. In one example, this includes obtaining imaging data of a patient's brain using an imaging modality, such as computed tomography (CT) or magnetic resonance (MR) imaging modalities, for example, or another suitable imaging modality. The anatomic volume need not be all or part of the patient's brain, but could be all or part of any other anatomic structure.

At 302, in one example, diffusion tensor imaging (DTI) data is obtained (this may occur at 300, such as where a DTI MR imaging modality is used at 300). In one example, the DTI data is obtained from the same patient being analyzed. Alternatively, "atlas" DTI data is obtained from at least one other patient. If atlas DTI data from another patient is used, it is typically spatially scaled to correspond to the anatomic size and shape of the patient being analyzed. In one example, the atlas DTI data is based on a composite from more than one other patient. The composite atlas DTI data typically spatially scales DTI data from the different patients before combining into the composite DTI atlas. The atlas DTI data avoids the need to obtain DTI data from the particular patient being analyzed. This is useful, for example, when a non-DTI imaging modality is used at 300.

At 304, a tissue conductivity model is created for all or part of the anatomic volume. The tissue conductivity model is typically a non-uniform spatial distribution. Such a model more accurately represents inhomogeneous and anisotropic characteristics of the tissue anatomy. For example, the conductivity of brain tissue varies from one brain region to another. Moreover, conductivity of the nervous system is preferential to a particular direction that is also dependent on the particular location in the brain. In one example, a non-uniform tissue conductivity model is created by transforming the DTI data into conductivity data, such as by using the linear transform techniques discussed above with respect to Equation 2.

It should be noted that it is not required to obtain non-uniform tissue conductivity data using DTI. There exist several alternatives to using DTI based approximations for the anisotropic and inhomogeneous tissue properties for the patient specific finite element volume conductor model. One example technique would be a simple designation of a white matter and a grey matter conductivity tensor. These two universal conductivity tensors could then be applied to the nodes of the FEM mesh using co-registration with the anatomical MRI. In this manner, the individual voxels of the MRI data are designated as either white matter or grey matter using post-processing image analysis. Then, each such voxel is assigned a conductivity dependent on whether it was classified as white matter or grey matter, which white matter voxels having a different conductivity value than grey matter voxels. A second example technique would define individual conductivity tensors for designated brain regions (e.g., nuclei, sub-nuclei, fiber tracts, etc.). This method would allow for a more detailed representation of the tissue electrical properties than the first example technique. The conductivity tensor of each designated brain region is defined, in one example, using explicit experimental tissue impedance results and anatomical information provided by a human brain atlas. In this technique, the anatomical MRI is sub-divided into different designated brain regions on a voxel-by-voxel basis using post-processing image analysis. The appropriate conductivity tensors for each designated brain region is then co-registered with the nodes of the FEM mesh.

At 306, a finite element model (FEM) is created using the conductivity data obtained at 304. In one example, the FEM model uses a default boundary condition that is appropriate for a typical electrode contact morphology. However, in another example, the FEM model includes an electrode-specific boundary condition that is tailored to the morphology of a particular electrode contact or contacts to be used in the DBS or other procedure. The FEM model provides for non-uniform conductivity in the tissue, such as by using a DTI-derived other conductivity value at each node in the FEM mesh. The FEM model may include aspects that are not obtained from the DTI-derived data. In one such example, the FEM mesh models a thin encapsulation sheath about the electrode lead body, as discussed above, which is not derived from the DTI data.

At 308, in one example, the FEM is solved for the electric potential distribution or the second difference ($\Delta^2 V$) of the electric potential distribution, as discussed above, such as by using FEM solver software. In one example, the FEM is solved for a normalized stimulation amplitude of 1V. In another example, for a different electric stimulation amplitude, the resulting electric potential distribution (or second difference of the electric potential distribution) is multiplied by a scale ratio of the different electric stimulation amplitude to the normalized electric stimulation amplitude.

At 310, a volume of activation (VOA) or other volume of influence is calculated, in one example, using the second difference of the electric potential distribution. The VOA represents the region in which any neurons therein are expected to typically be activated, that is, they are expected to generate propagating action potentials at the stimulus frequency in response to the electrical stimulation delivered at the stimulation electrode contact. Conversely, neurons outside the VOA are expected to typically remain unactivated in response to the electrical stimulation. In one example, a particular threshold value of the second difference of the electric potential distribution defines the boundary surface of the VOA.

As discussed above, the particular threshold value defining the boundary of the VOA is determined as follows. First, model neuronal elements are positioned relative to the electrode using known neuroanatomical information about specific fiber pathways and nuclei of interest near the electrode. These generalized positions of the model neuronal elements are then refined, such as by using explicit "patient-specific" information provided in the DTI or anatomical MR imaging data. For example, the DTI imaging data describes the inhomogeneous and anisotropic tissue properties near the electrode. In this example, such DTI imaging data is used to explicitly define one or more axonal trajectories, if needed, or to help define nuclear boundaries specified in the anatomical MR.

A model of these neurons is then created. In one example, the neurons are modeled using an axon model, which is a simplified form of a neuron model. An example of an axon model is described in Cameron C. McIntyre et al., "Modeling the Excitability of Mammalian Nerve Fibers: Influence of Afterpotentials on the Recovery Cycle," J. Neurophysiology, Vol. 87, February 2002, pp. 995-1006, which is incorporated by reference herein in its entirety, including its disclosure of axon models. In another example, a more generalized neuronal model is used, an example of which is described in Cameron C. McIntyre et al., "Cellular Effects of Deep Brain Stimulation: Model-Based Analysis of Activation and Inhibition," J. Neurophysiology, Vol. 91, April 2004, pp. 1457-1469, which is incorporated by reference herein in its entirety, including its disclosure of neuronal models. The neuron model describes how the neurons will respond to an applied electric field, that is, whether the neuron will fire and whether the neurons will generate a propagating action potential.

In one example, using this neuron model to simulate how the neurons (located as determined from the DTI-derived conductivity data, in one example) behave, the threshold value of the second difference of electric field that will result in such propagating action potentials is calculated. The stimulating influence of the electric field is applied to the model neurons to define a threshold value. This threshold value is then used to define the boundary of the VOA in the non-uniform conductivity tissue, as discussed above.

It should be noted that the neuron model may depend on one or more of the electrical parameters of the DBS stimulation being modeled. For example, the stimulation pulsewidth will affect the neuron response. Therefore, in one example, the neuron model is tailored to a specific value for one or more DBS stimulation parameters.

It should also be noted that calculation of explicit threshold criteria for each patient is not required. For example, in a more generalized situation, threshold criteria will have already been determined using the detailed neuron models under a wide variety of different stimulation conditions. Once these threshold criteria have been determined, they need not be re-determined for each subsequent patient.

It should also be noted that using a threshold criteria upon the second difference of the potential distribution in the tissue medium is a simplified technique for quickly determining a VOA or other volume of influence. The intermediate step of using the second difference of the potential distribution is not required. In an alternate example, the FEM model of is directly coupled to a detailed neuron model, such as a multi-compartment neuron model that is oriented and positioned in the FEM model to represent at least one actual nerve pathway in the anatomic volume.

At 312, the calculated VOA region is displayed, such as on a computer monitor. In one example, the VOA is displayed superimposed on the displayed imaging data or a volumetric representation derived from such imaging data. In another example, an anatomic boundary or other representation of an anatomic structure is superimposed on the VOA and imaging data or the like. The anatomic boundary data is typically obtained from an atlas of brain anatomy data, which can be scaled for the particular patient, as discussed above. Alternatively, the anatomic representation is extracted from the imaging data for the patient being analyzed. In one example, the anatomic representation is a line depicting one or more boundaries between particular nucleus structures or other regions of the brain, such as the STN, IC, or ZI illustrated above in FIG. 1B.

In any case, by viewing a representation emphasizing one or more brain regions displayed together with the VOA, the user can then determine whether a particular anatomic region falls within or outside of the modeled VOA. The user may want a particular anatomic region to be affected by the DBS, in which case that region should fall within the modeled VOA. Alternatively, the user may want a particular region to be unaffected by the DBS, such as to avoid certain unwanted DBS stimulation side effects, as discussed above. This evaluation of whether the VOA is properly located can alternatively be performed by, or assisted by, a computer algorithm.

For example, the computer algorithm can evaluate various VOAs against either or both of the following input criteria: (a) one or more regions in which activation is desired; or (b) one or more regions in which activation should be avoided. In one example, at 314, the computer algorithm creates a score of how such candidate VOAs map against desired and undesired regions. In one example, the score is computed by counting how many VOA voxels map to the one or more regions in which activation is desired, then counting how many VOA voxels map to the one or more regions in which activation is undesired, and subtracting the second quantity from the first to yield the score. In another example, these two quantities may be weighted differently such as, for example, when avoiding activation of certain regions is more important than obtaining activation of other regions (or vice-versa). In yet another example, these two quantities may be used as separate scores.

At 316, the score can be displayed to the user to help the user select a particular VOA (represented by a particular electrode location and parameter settings). Alternatively, the algorithm can also automatically select the target electrode location and parameter settings that provide the best score for the given input criteria.

In one example, the VOA is displayed on a computer display monitor of an image-guided surgical (IGS) workstation, such as the StealthStation® from the Surgical Navigation Technologies, Inc. (SNT) subsidiary of Medtronic, Inc., for example. The VOA can be displayed on the IGS workstation monitor with at least one of the imaging data representing the anatomic volume, the target electrode location, a burr hole or other anatomic entry point, a trajectory between the anatomic entry point and the target electrode location, or an actual electrode location.

In one IGS workstation example, the displayed VOA corresponds to a target electrode location. Another IGS workstation example provides an intraoperatively displayed VOA corresponds to an actual electrode location of an electrode being introduced along the trajectory. The VOA is recomputed and redisplayed as the electrode is being introduced along the trajectory, such as by using position information tracking the position of the electrode being introduced. In one example, various VOAs along the trajectory are pre-computed, and the particular VOA is selected for display using the tracked position of the electrode as it is being introduced.

After the electrode is positioned at the target location, it is typically secured in place, such as by using a lead immobilizer located at the burr hole or other anatomic entry point. There remains the challenging task of adjusting the DBS stimulation parameters (e.g., the particular electrode contact(s) of a plurality of electrode contacts disposed on the same DBS leadwire, pulse amplitude, pulsewidth, electrode "polarity" (i.e., monopolar or bipolar electrode return path), electrode pulse polarity (i.e., positive or negative), frequency, etc.). In one example, the IGS workstation or a DBS pulse generator programmer includes the above-described VOA methods to assist the user in selecting an appropriate combination of DBS stimulation parameters, such as by using the scoring techniques discussed above.

Figure 4:
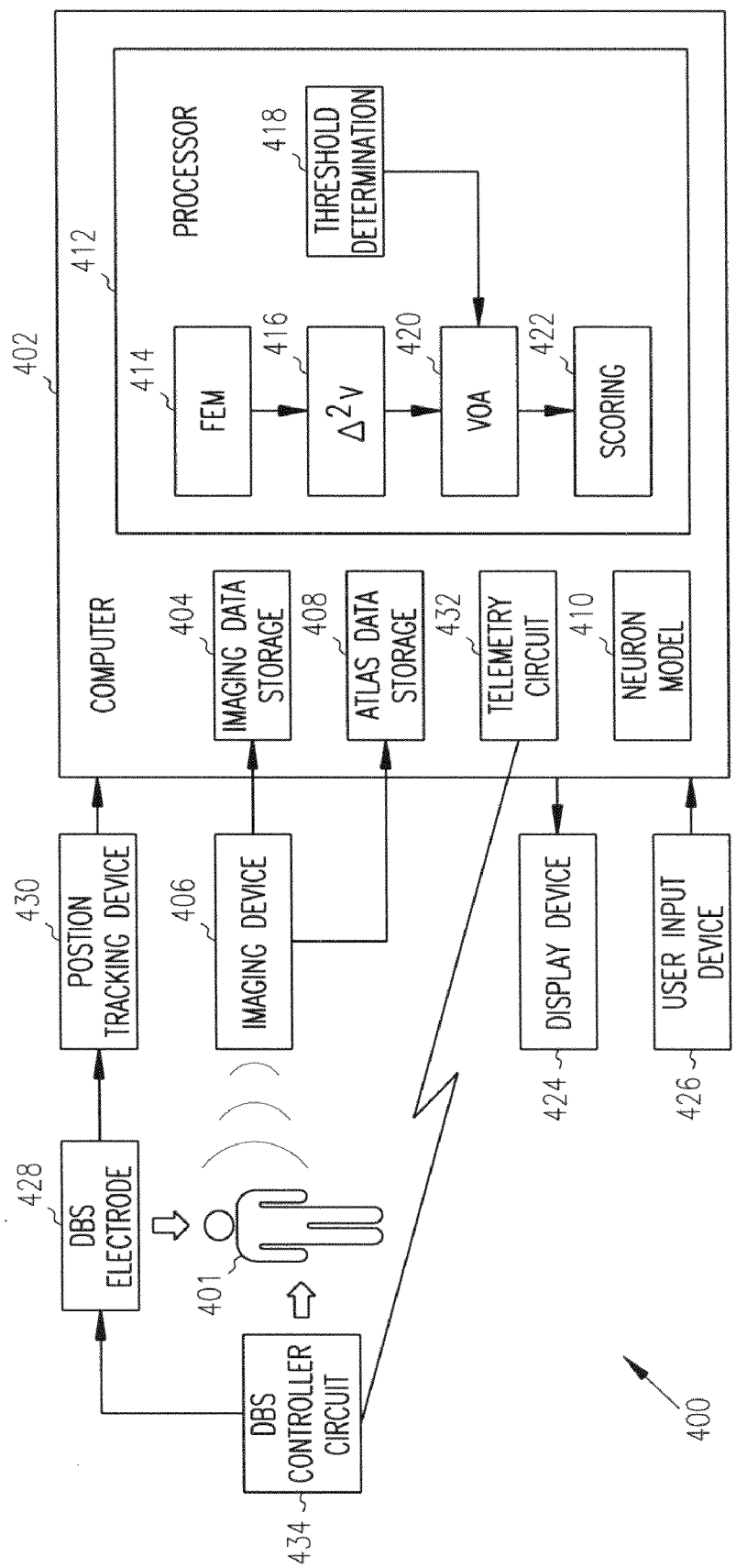
FIG. 4 is a block diagram illustrating generally one conceptualization of a system for performing at least some of the methods for deep brain stimulation (DBS) or other stimulation of a patient.

FIG. 4 is a block diagram illustrating generally one conceptualization of a system 400 for performing at least some of the methods discussed above for DBS or other stimulation of a patient 401. In this example, the system 400 includes an IGS workstation or other computer 402. The computer 402 includes imaging data storage 404 receiving imaging data from a medical imaging device 406. In this example, the computer 402 also includes DTI or other atlas data storage 408, and a neuron or axon model 410, as discussed above. A processor 412 uses a finite element model (FEM) 414 to compute a second difference 416 on an electric potential distribution. A threshold determination module 418 is used to develop a threshold value of the second difference 416 of the electric potential distribution to compute a volume of activation (VOA) 420, as discussed above. The processor 412 also includes a scoring module to compare the VOA against one or more desired or undesired anatomic regions, as discussed above, to determine whether the VOA will perform as desired. In one example, the VOA is displayed on a display device 424, such as together with other data that is typically displayed on an IGS workstation display, as discussed above. A user input device 426 permits a user to input data, for example, particular information about the configuration or morphology of the DBS or other stimulation electrode 428 being used in the procedure. In one example, a position tracking device 430 tracks the location of the DBS electrode so that the location can be displayed on the display device 424, such as with the VOA or scoring information discussed above. In a further example, the computer 402 includes a telemetry circuit 432 for programming or otherwise communicating with an implantable DBS controller circuit 434, such as to adjust electrical stimulation parameters using the VOA or scoring information discussed above. Although FIG. 4 illustrates an IGS workstation example, it is understood that portions of the system 400 could alternatively be implemented outside the context of an IGS workstation such as, for example, in an external programmer device for an implantable DBS controller circuit 434. Such an alternate example need not include any intraoperative imaging or position tracking.

Figure 5:
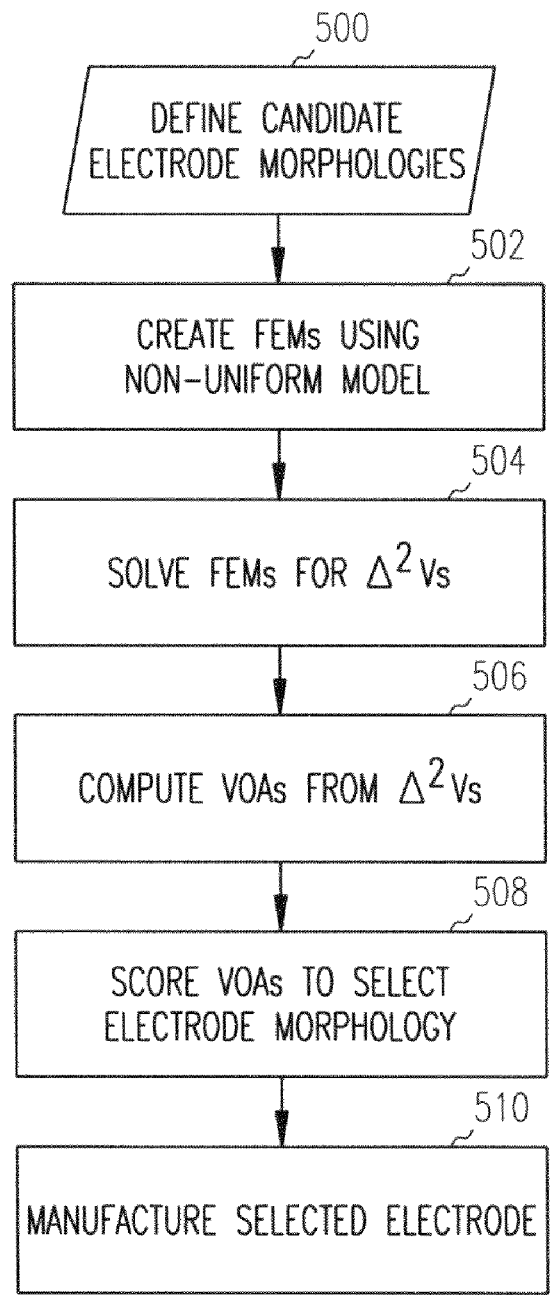
FIG. 5 is a flow chart illustrating generally one example of a method of using a model to calculate a volume of activation (VOA), and using the VOA to select a particular electrode morphology.

FIG. 5 is a flow chart illustrating generally one example of a method of using a model to calculate a volume of activation, as discussed above, and using the VOA to select a particular electrode morphology. Portions of the method may be embodied in any machine-accessible medium carrying instructions for executing acts included in the method. Such a method applies to selecting an electrode morphology for deep brain stimulation (DBS) or for any other electrical tissue stimulation. At 500, a set of N candidate electrode morphologies are defined, where N is an integer greater than 1. Defining the candidate morphologies typically includes providing information about the size, shape, or arrangement of electrode contacts on a leadwire. Such information is typically in a form in which it can be used as input to a finite element model (FEM). At 502, a FEM is created for each candidate electrode morphology. The FEMs typically use non-uniform conductivity model of a desired region of interest, as discussed above. At 504, each FEM is solved for a second difference in the electric potential distribution, as discussed above. At 506, a volume of activation (VOA) is computed for each candidate electrode morphology from its corresponding second difference in the electric potential distribution. The boundary of the VOA is typically obtained from a threshold value that is based on a neuron or axon model, as discussed above. At 508, the VOAs are scored, as discussed above, or otherwise evaluated to select one or more electrode morphologies that exhibit a desired VOA, or a VOA that is deemed more desirable than the VOA of one or more other electrode morphologies. At 510, at least one electrode is manufactured using the selected at least one electrode morphology.

3. Application in a Patient-Specific Neural Stimulation Modeling System

A. Overview

One application of the above-described neural response modeling techniques is in a patient-specific neural stimulation modeling system (PSNSMS), which can be implemented as a software package that, in one example, can be integrated into an IGS workstation or any other desired computer implementation. The PSNSMS allows interactive manipulation of patient-specific electrical models of the brain for analysis of brain stimulation methods. This provides a virtual laboratory for surgeons, technicians, or engineers to optimize or otherwise adjust neural stimulation treatment, such as by varying electrode position, stimulation protocol, or electrode design. In one example, the PSNSMS integrates data processing, numerical solution and visualization into one cohesive platform. In one example, the PSNSMS uses a modular framework that incorporates anatomical or functional magnetic resonance images, 3D geometric models of individual brain nuclei, volume conductor models of the electric field generated by the stimulation, biophysical models of the neural response to the stimulation, numerical solutions of the coupled electric field and neuron models, and 3D visualization of the model results and imaging data. Among other things, the PSNSMS outputs a volume of influence (neural activation or neural inhibition) generated by the stimulating electrode for a given position in the brain and given stimulation parameters.

Benefits of the PSNSMS may include, among other things: (1) pre-operative targeting of an optimal or desirable neural stimulation electrode position or trajectory in the brain tissue medium; (2) intra-operative monitoring or visualization of electrode position or trajectory and stimulation effects as a function of the stimulation parameters; (3) post-operative adjustment or optimization of one or more stimulation parameters for therapeutic benefit given knowledge of the actual electrode position in the brain; or (4) a design tool for evaluating or testing different electrode designs, such as for a given anatomical target.

Existing techniques for pre-operatively targeting specific nuclei for neurostimulation using magnetic resonance imaging data only account for certain anatomical considerations. They typically ignore the electric field generated by the stimulation and the subsequent neural response to the stimulation. Existing techniques for intra-operatively monitoring the electrode position in the brain, based on the spontaneous electrical activity of neurons surrounding the electrode, require highly skilled neurophysiologists to interpret the data. Moreover, such techniques are not linked with 3D visualization of the surrounding neuroanatomy. Furthermore, they do not enable prediction of the effects of stimulation as a function of the stimulation parameters. Existing techniques for defining effective stimulation parameter values typically rely on trial and error. They typically do not explicitly take into account the anatomical position of the electrode or the neural response to stimulation as it depends on changes in the stimulation parameters. Moreover, they typically do not use any optimization strategies to define the stimulator parameter settings.

The PSNSMS addresses these and other limitations. In one example, the PSNSMS uses a finite element model (FEM) of the electric field generated by the stimulation. In one example, the tissue electrical properties of the FEM are based on diffusion tensor magnetic resonance imaging analysis, also referred to as diffusion tensor imaging (DTI). DTI permits explicit characterization of the inhomogeneous and anisotropic tissue properties near a given electrode position. The inhomogeneous and anisotropic tissue properties distort the electric field. Therefore, they are important to consider when addressing the neural response to the stimulation.

In one example, the electric field model is then coupled to electrical models of individual neurons to predict their response to the applied stimulation and determine a volume of tissue that is directly influenced by the stimulation. In another example, simplifying assumptions allow the volume of activation (VOA) to be obtained directly from the electric field model using the second difference of the potential distribution in the tissue medium, as discussed above.

The PSNSMS also allows integration of MR imaging data, 3D anatomical volumes, neural stimulation electrode trajectory, and 3D neural stimulation response volume in a single platform or package. This platform or package can be used for, among other things, pre-operative targeting, intra-operative monitoring, post-operative stimulation parameter adjustment or optimization, or electrode design. One example of such a package is a image-guided surgical (IGS) workstation, which typically displays voxel data obtained from MR or CT images, and to which a display of a modeled 3D neural stimulation response volume of influence (or other information obtained from a modeled 3D neural stimulation response volume of influence) has been added.

B. Exemplary Methods

In one example, the PSNSMS allows, among other things, capture of the detailed interaction between the electric field and underlying non-uniform tissue medium. This enables more accurate estimation of the spatial extent of neural activation generated by one or more electrodes implanted in the nervous system. In one embodiment, the PSNSMS includes the following components: (1) a volume conductor electric field model such as a FEM mesh, which includes a model of the stimulating electrode and of any inhomogeneous and anisotropic electrical properties of nearby tissue; (2) one or more multi-compartment electrical models of individual neurons whose positions can be specified within the electric field (e.g., using anatomically-derived conductivity data to ascertain the locations of neural pathways) and their response to stimulation can be quantified; (3) integration of functional or anatomical imaging data into a visualization platform that can be combined with the electric field modeling results; or, (4) techniques to determine a desired or optimal electrode position or one or more desired or optimal stimulation parameters on a patient-specific basis.

Figure 6:
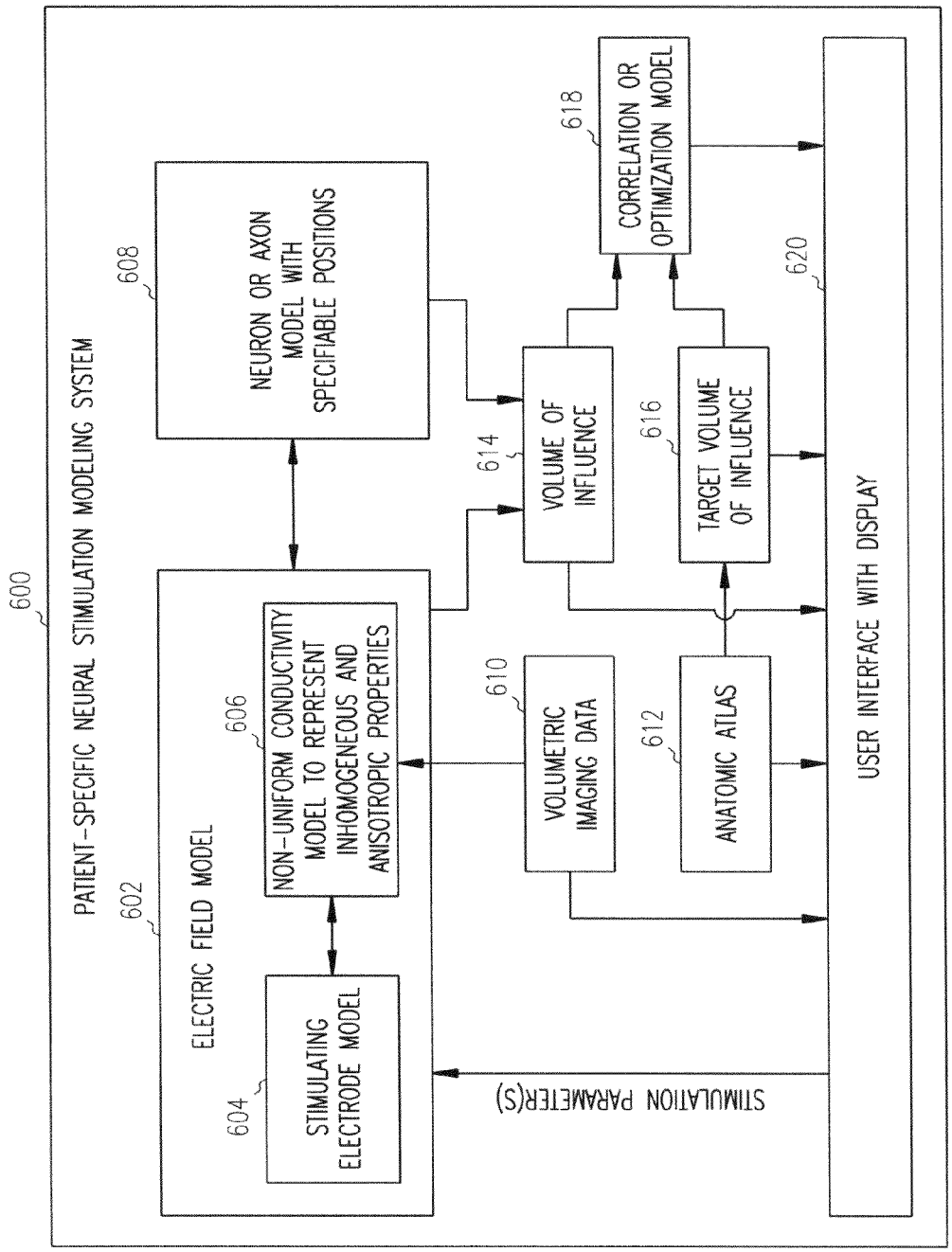
FIG. 6 is a block diagram illustrating generally one example of a computer-assisted patient-specific neural stimulation modeling system.

FIG. 6 is a block diagram illustrating generally one example of such a computer-assisted patient-specific neural stimulation modeling system 600. In this example, the system 600 includes an electric field model 602. In one example, the electric field model 602 is implemented as a computer-solvable FEM mesh. It typically includes a stimulating electrode model 604. The stimulating electrode model 604 typically represents the morphology of the particular stimulation electrode. It may also include a representation of the conductivity of a thin layer of tissue encapsulating the particular electrode. The electric field model 602 also includes non-uniform tissue conductivity data 606. Such data represents any inhomogeneous or anisotropic properties of the tissue near the stimulation electrode, and can be obtained by DTI imaging or by using other techniques described elsewhere in this document.

In the example of FIG. 6, the system 600 also includes a neuron or axon model 608. In one example, a multi-compartment neuron or axon model positions the modeled neurons or axons at specifiable positions along one or more nerve pathways in the FEM mesh. Such nerve pathways can be ascertained using the DTI-derived imaging data, or by using anatomic atlas data, or any other technique. The example of FIG. 6 also includes stored volumetric imaging data 610 and volumetric anatomic atlas data 612. Using a computer FEM solver to solve the electric field model 602, together with the neuron or axon model 608 (optionally using the intermediate step of solving for a second difference in the electric potential distribution) a volume of influence 614 is calculated. The volume of influence 614 typically represents a volume of activation of region, but could also represent a volume of inhibition region. The model-computed volume of influence 614 is then compared to a target volume of influence 616, which, in one example, is specified by user input that is referenced to the anatomic atlas 612. In one example, a correlation between the two is computed at 618. In a further example, several model-computed volumes of influence (e.g., using different electrode locations or parameter settings) are computed and correlated to the target volume of influence, such as to optimize or otherwise select a desirable electrode location or stimulation parameter settings. The system 600 includes a user interface with a display, such as to display the volume of influence in conjunction with the volumetric imaging data 610, which may be annotated or segmented using anatomic boundaries obtained from the anatomic atlas 612, or otherwise. In one example, the display also provides an indication of information regarding the correlation or the optimization.

Our example demonstration of PSNSMS is based on deep brain stimulation (DBS) of the subthalamic nucleus (STN), but the concepts described in this document are transferable to any electrode design or to stimulation of any region of the nervous system. In one example, one or more portions of the PSNSMS is constructed using the shareware package SCIRun with BioPSE (Scientific Computing and Imaging Institute, University of Utah), which provides an integrated environment for data manipulation, analysis, and interactive visualization.

C. Volume Conductor Electric Field Model Example

Figure 7:
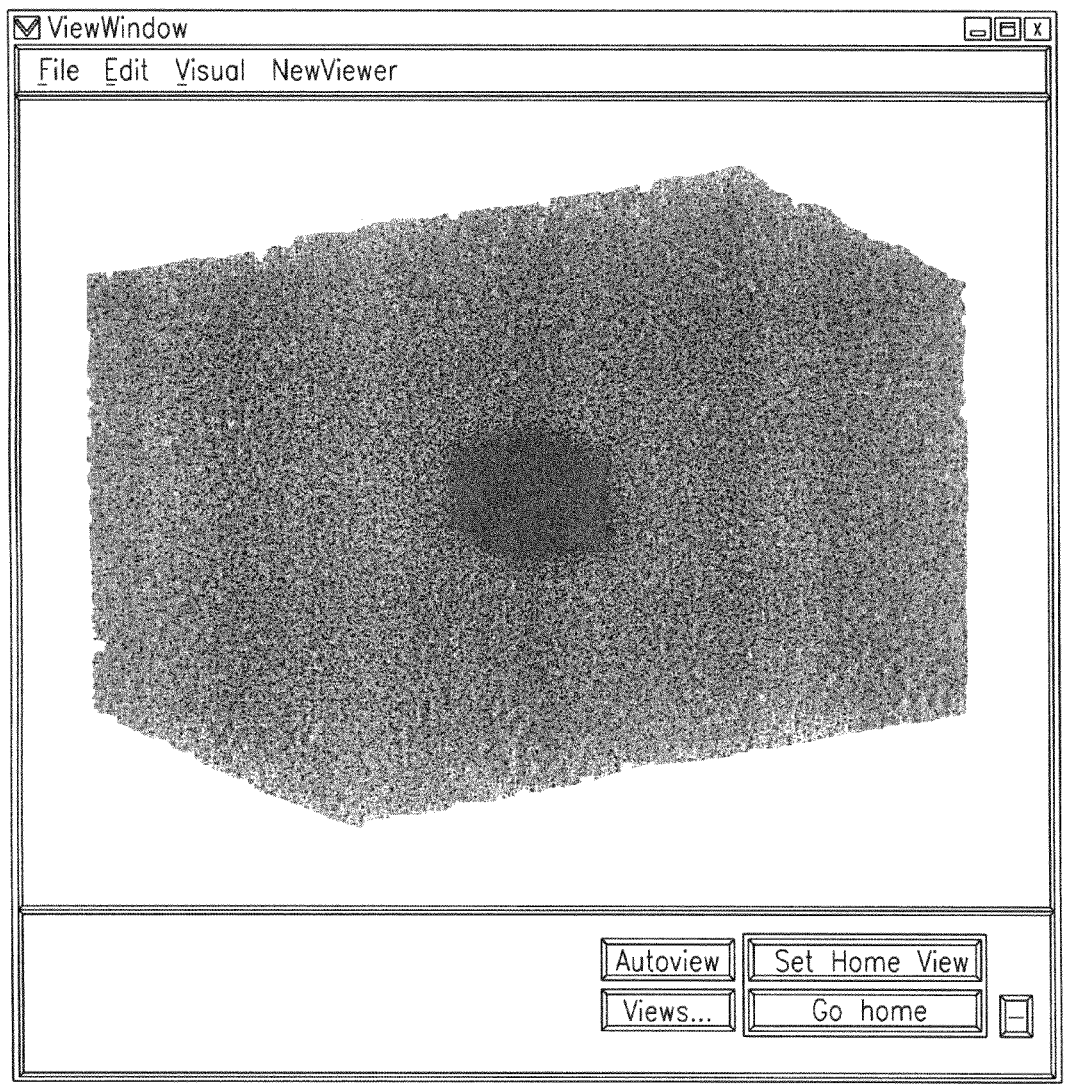
FIG. 7 is a computer display screenshot illustrating one example of a multi-resolution, finite-element tetrahedral mesh.
Figure 8:
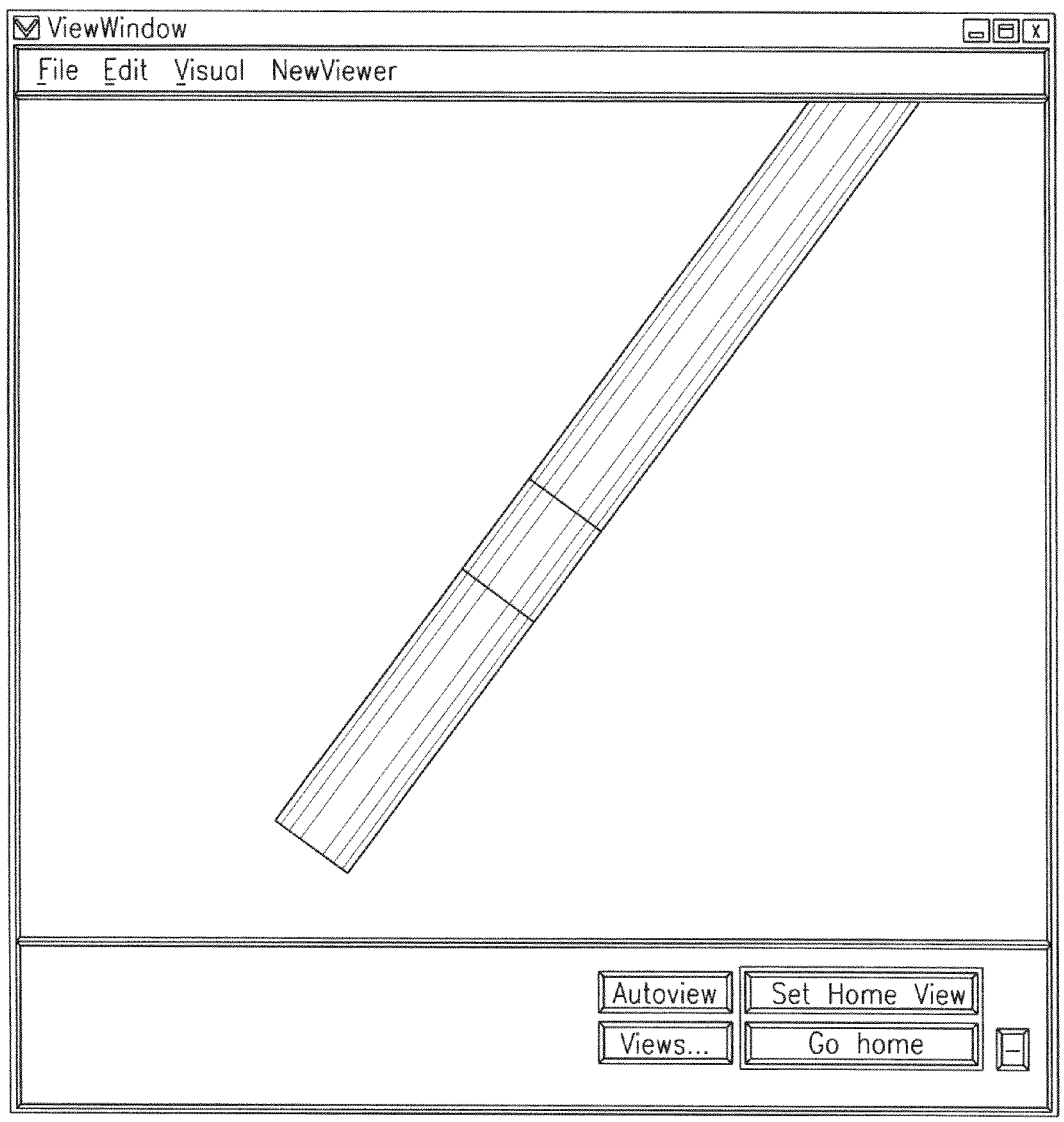
FIG. 8 is a computer display screenshot illustrating one example of a stimulation electrode shaft.

In one example, detailed patient-specific electric field models of central nervous system stimulation were developed using anatomical and diffusion tensor magnetic resonance data (DTI). FIG. 7 is a computer display screenshot illustrating one example of a multi-resolution, finite-element tetrahedral mesh that was constructed to represent the brain volume near the electrode shaft in the computer display screenshot of FIG. 8. The example of FIG. 7 illustrates a generic mesh that includes a high density mesh around the electrode location and a low density mesh located between the high density mesh and the model's peripheral boundary. The finite element method (FEM) allows complex geometric structures to be accurately represented where analytical solutions are complex or fail to exist. The multi-resolution method illustrated in FIG. 7 provides a dense enough mesh to accurately compute the FEM solution near the electrode, but reduces the size of the system of equations enough to allow interactive solution of the FEM, such as to experiment with different stimulation parameters or electrode locations. The accuracy of the solution for a given mesh density can be estimated using the L2 norm, and the mesh can be refined as needed.

In one example, the DTI data was used to estimate the inhomogeneous and anisotropic tissue conductivity properties on a patient-specific basis and this information was integrated into the FEM. As described above, the electrical conductivity tensor ($\sigma$) was determined from the diffusion tensor (D) at each voxel of the DTI, such as by using Equation 2.

After a pre-operative electrode target location or post-operative implanted electrode location is determined, in one example, the volumetric conductivity data from the DTI (also referred to as a DTI voxel map) is co-registered with the FEM illustrated in FIG. 6. Thus, the orientation of the coordinate systems of the DTI voxel map and the FEM need not be the same. In one example, the coordinate system of the FEM illustrated in FIG. 7 is defined with its origin at the electrode contact and its Z-axis extending along the electrode shaft illustrated in FIG. 8. The coordinate system of the DTI voxel map is determined by the patient head position in the imaging scanner. However, conductivity tensor data is not rotationally invariant. Therefore, in one example, a DTI-based conductivity tensor is rotated from its original acquisition reference frame to the electrode reference frame, such as by extracting the electrode angle with respect to the axial ($\alpha$) and sagittal ($\beta$) planes using post-operative anatomical imaging results. In turn, the conductivity tensor used in the FEM (i.e., $\sigma'$) is of the form:

$$\sigma' = R\sigma R^T \quad \text{(Eq. 3)}$$

where R is the rotation matrix for the image transformation defined by $\alpha$ and $\beta$.

After this transformation, each node of the FEM mesh is assigned a conductivity tensor that is mapped to its corresponding location within the DTI voxel map. In one example, the FEM mesh illustrated in FIG. 7 serves as a template structure that can read in C for each node of the FEM mesh from a generic DTI voxel map data set. This template allows a single model geometry and FEM mesh (the most difficult and time consuming components of FEM development) to be used for each patient-specific model and/or for each candidate electrode location to which each patient-specific model is applied.

Figure 9:
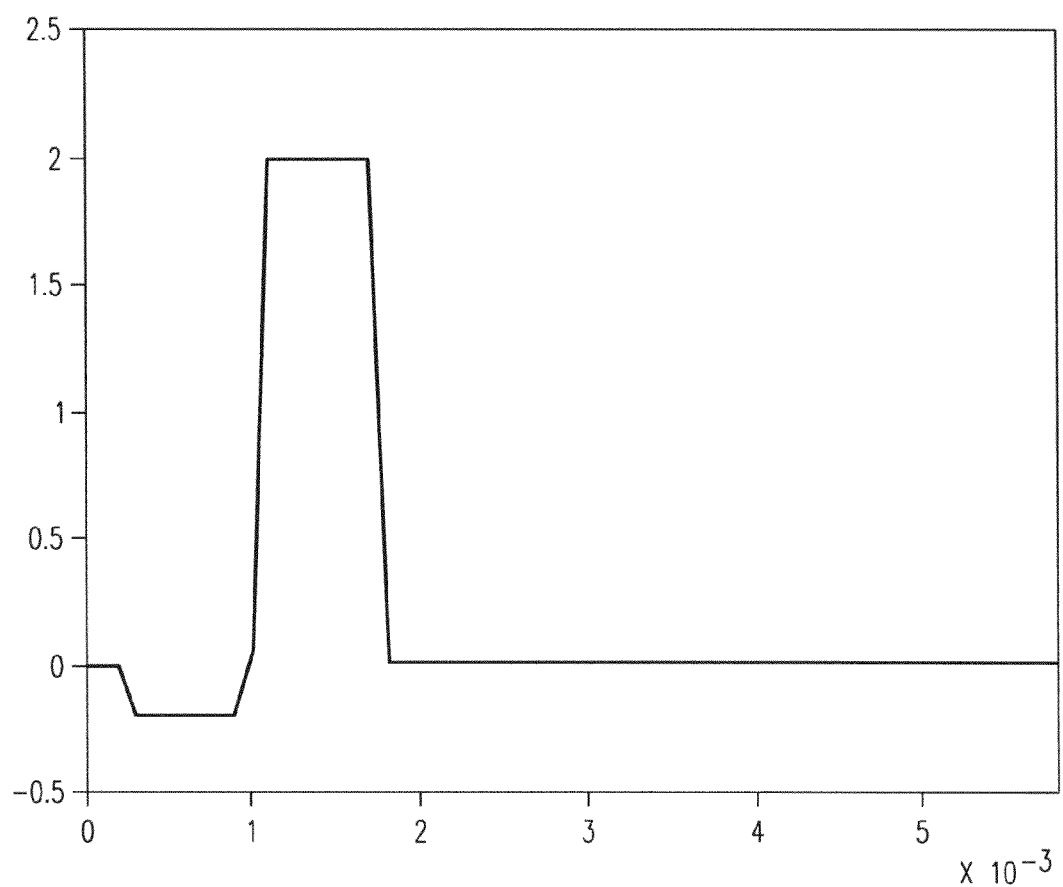
FIG. 9. is a voltage vs. time graph of an exemplary stimulation waveform.

After the FEM is defined with the appropriate tissue conductivity data, appropriate boundary conditions are set, as discussed above. Then, Equation 1 is solved to determine the electric potential distribution generated in the tissue medium. Equation 1 is typically solved using one of two solvers, depending on the characteristics of the stimulation waveform used, an example of which is illustrated in voltage amplitude vs. time graph of FIG. 9. For steady-state analysis, when the quasi-static approximation is valid, the system is typically solved using a conjugate gradient solver and constant voltage stimulation. However, if the quasi-static approximation is not valid and bulk capacitance is to be taken into account, then the system is typically solved using a Fourier FEM solver using a time-dependent stimulation waveform. The Fourier FEM solver decomposes the stimulus waveform into a collection of sine waves, each with known amplitude and phase. These sinusoidal sources are added to the right hand side of Equation 1, and complex impedances are added to the stiffness matrix (that is, the conductivity tensor ($\sigma$)). The system of equations is then solved for each component frequency using a complex solver. By virtue of linear superposition (i.e., the solutions at different frequencies do not significantly interact) and assuming small currents (i.e., there is no significant coupling between magnetic and electric fields), the solution for an arbitrary waveform can be found by summing the time-domain solutions at each frequency. Solving Equation 1 yields a record of the potential at each node in the FEM mesh as a function of time during the applied stimulation.

D. Example of Quantifying the Neural Response to Stimulation

Knowing the potential distribution in the tissue medium alone is not enough to predict the neural response to stimulation. Therefore, in one example, we use one or more multi-compartment cable models of individual neurons to address the neural response to the stimulation. Such neuron models represent electrically equivalent circuit representations of physiological neural signaling mechanisms. The models typically include an explicit representation of the complex neural geometry and individual ion channels that regulate generating of action potentials. The neuron model geometries are typically broken up into many (e.g., hundreds) of compartments and are co-registered within the FEM mesh. This allows calculation of the extracellular potentials from the applied electric field along the complex neural geometry. After the extracellular potentials are determined for each neural compartment as a function of time during the applied stimulation, for each neural position relative to the electrode, the model neuron is used to test whether the applied stimulus exceeded the neural threshold that triggers an action potential. The neural response to extracellular stimulation is dependent on several factors, such as, for example: (1) the electrode geometry; (2) the shape of the electric field (as determined by the inhomogeneous and anisotropic bulk tissue properties); (3) the neuron geometry; (4) the neuron position relative to the stimulating electrode; (5) the neuron membrane dynamics; and, (6) the applied stimulation parameters (e.g., stimulus waveform, stimulation frequency, etc.).

In one illustrative example, we used the 5.7 μm diameter double cable myelinated axon model described in Cameron C. McIntyre et al., "Modeling the Excitability of Mammalian Nerve Fibers: Influence of Afterpotentials on the Recovery Cycle," J. Neurophysiology, Vol. 87, February 2002, pp. 995-1006, which is incorporated herein by reference in its entirety. (Alternatively, instead of using an axon model, a more detailed neuronal model could be used, such as described in Cameron C. McIntyre et al., "Cellular Effects of Deep Brain Stimulation: Model-Based Analysis of Activation and Inhibition," J. Neurophysiology 91: 1457-1469 (2004), which is incorporated by reference herein in its entirety). We incorporated this model into our STN DBS FEM to quantify the neural response to stimulation. By positioning the axon in different locations relative to the electrode and modulating the stimulation parameters one can determine the threshold stimulus necessary to activate the neuron. Likewise, for a given stimulation parameter setting (pulse duration, amplitude, frequency), the threshold characteristics of the model neuron can be determined as a function of space around the electrode. This information defines of a volume of tissue for which the neural activation threshold is exceeded for the particular stimulation parameter setting. This volume of tissue is referred to as the volume of activation (VOA). In one example, a further simplification is made by determining a threshold value of the second difference of the potential distribution, which is representative of neural activation for a given stimulation parameter setting, as discussed above and as illustrated in FIG. 2. The threshold second difference value can then also be used to define the VOA boundaries.

When using PSNSMS to pre-operatively characterize stimulation effects, assumptions are typically made as to the appropriate model parameter values used to predict the volume of activation. However, during post-operative use, the PSNSMS model can be fit to patient-specific experimental threshold results. The tissue conductivity and electrode localization for each patient-specific FEM can be adjusted to match the clinically determined threshold stimulation results for activating major fiber tracts near the electrode. Detecting fiber tract activation may involve monitoring behavioral responses that are known to arise from such activation of specific fiber tracts. The clinical threshold to elicit these behavioral responses is determined. These fiber tracts can be explicitly visualized on the DTI voxel map. The location and trajectory of particular fiber tracts can be directly integrated into PSNSMS by positioning the axon models along the appropriate anatomical trajectory in the FEM. Three general variables can be adjusted to fit the FEM to the experimental data. First, the conductivity of the encapsulation layer about the electrode can be adjusted (e.g., $0.2$ S/m$<\sigma_{encap}<0.1$ S/m) to fit the FEM to the experimental data. Alterations in this variable modulate the electrode input impedance. Such adjustments can be guided by clinical data from the stimulator programming unit. Second, the ratio of effective extracellular conductivity and the effective extracellular diffusivity ($0.6<\sigma_e/d_e<0.8$ (S–s)/mm$^2$) can be adjusted. Altering this variable scales the absolute value of the conductivity tensor and modulates the stimulus amplitudes needed for axonal activation. A third variable is the X, Y, Z position of the electrode relative to the tissue medium. We expect about 1 mm error in our MR-based electrode localization due to the metallic distortion artifact generated by the electrode in the MR image. Therefore, in one example, we allow the electrode to be shifted by a maximum of 0.5 mm in any direction to allow convergence between the model-predicted threshold data and the clinical threshold data.

Figure 10:
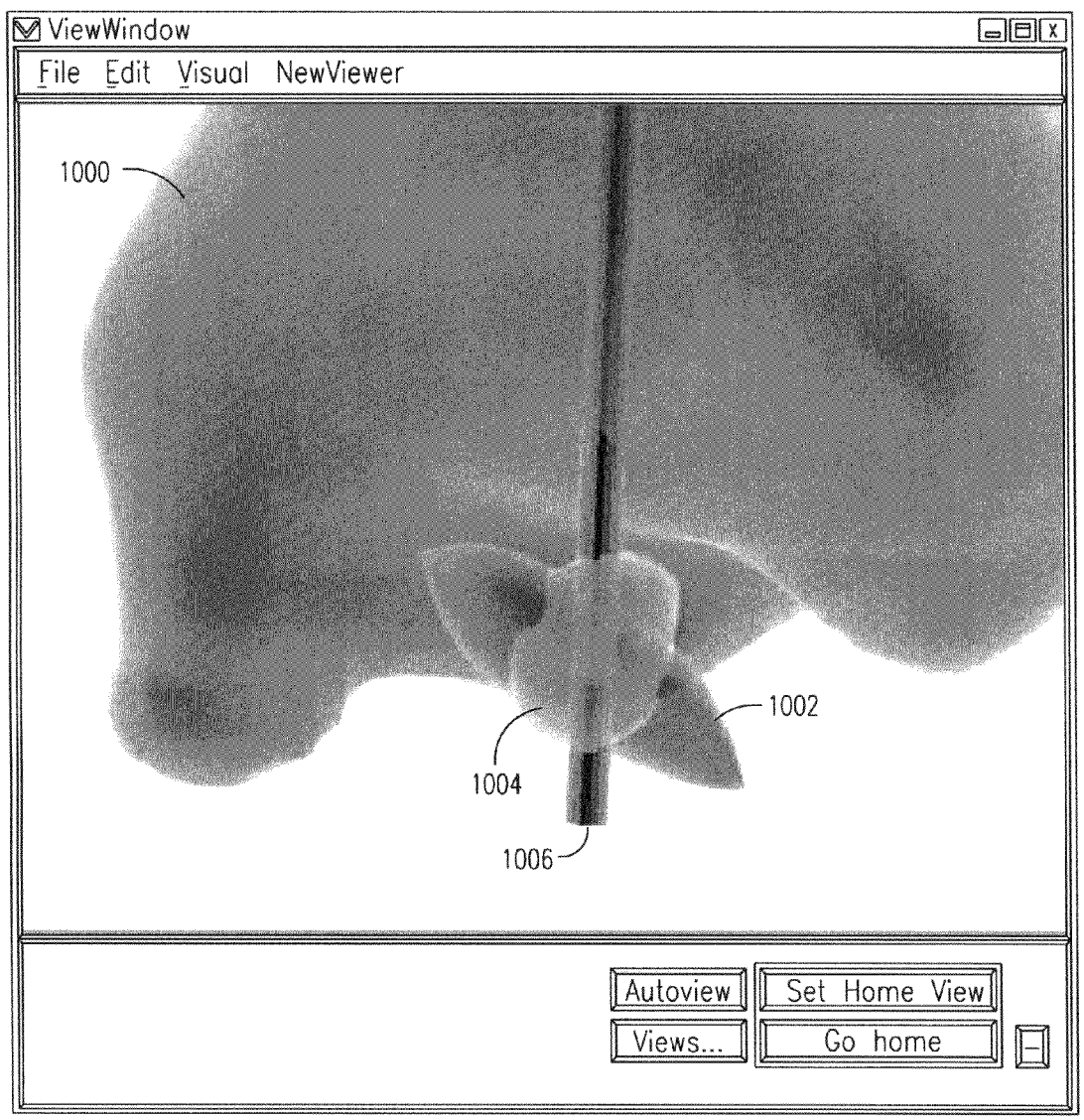
FIG. 10 is a computer display screenshot illustrating one example of a displayed the target region together with the model-calculated volume of influence.

E. Example of Integrating Stimulation Modeling Results and Anatomic Imaging Data Calculating the volume of activation as a function of the electrode location and stimulation parameters represents one component of PSNSMS. This provides even greater utility when it is integrated with patient-specific anatomical data. Anatomical data derived from MRI is commonly used to target stereotactic neurosurgical procedures. In one example, however, the PSNSMS integrates and displays the anatomical data with volume of activation data, as illustrated by the computer display screenshot of FIG. 10. In FIG. 10, the PSNSMS outputs a volume-rendered or other data display indicating one or more of: one or more non-target regions 1000 of the brain; the target region 1002 of the brain (in this case, the STN); or the volume of influence (e.g., volume of activation or volume of inhibition) 1004. In the example of FIG. 10, these also are coregistered to and displayed with the DBS electrode catheter 1006.

In one example, the PSNSMS includes a patient-specific brain atlas. Such atlases can be generated from the pre-operative anatomical MR images using techniques originally described by Gary E. Christensen et al., "Volumetric Transformation of Brain Anatomy," IEEE Trans. on Medical Imaging, Vol. 16, No. 6, pp. 864-877, December 1997, which is incorporated herein by reference in its entirety. However, any variety of morphing algorithms could be used. One suitable algorithm includes a nonlinear transformation to register one MRI (the patient-specific image) to a second pre-labeled target MRI that serves as a canonical atlas for particular regions of the brain. Segmentation of the patient-specific MRI is achieved by using the inverse of this transformation to warp the canonical atlas back onto the patient's 3D MR image. In one example, the registration procedure operates in two stages. In the first stage, a low-dimensional registration is accomplished by constraining the transformation to be in a low-dimensional basis. In one example, the basis is defined by the Green's function of the elasticity operator placed at pre-defined locations in the anatomy and the eigenfunctions of the elasticity operator. In the second stage, high-dimensional large transformations are vector fields generated via the mismatch between the template and target-image volumes constrained to be the solution of a Navier-Stokes fluid model. The result of these transformations is a 3D brain atlas matched to the individual patient with specific volumes representing pre-labeled target nuclei. The 3D surface data derived from the patient-specific brain atlas is then co-registered and, in one example, is displayed with the electrode and volume of activation data, as illustrated in the example of FIG. 10.

F. Example of Model-Based Selection of Patient-Specific Target Electrode Locations or Stimulation Parameter Settings One purpose of the PSNSMS is to determine optimal or desirable preoperative electrode locations or post-operative optimal or desirable stimulation parameters settings on a patient-specific basis. This typically involves determining a target volume of tissue that should be activated by the stimulation. In the PSNSMS, the geometry of this target VOA is typically determined based on the patient-specific 3D brain atlas. For example, in the case of STN DBS for Parkinson's disease, current anatomical and physiological knowledge indicate that the target volume of tissue is the dorsal half of the STN. Therefore, in this example, for each patient-specific 3D brain atlas we determine a target VOA defined by the dorsal half of the STN. We then determine test VOAs generated by a range of electrode positions within the STN and/or a range of stimulation parameter settings for each of those electrode locations. These test VOAs are then compared to the target VOA. The electrode position and/or stimulation parameter setting that generates a test VOA that most closely matches the target VOA is provided as the model-selected electrode position and/or stimulation parameter setting.

In one variant of this selection process, engineering optimization is used to assist the selection process. Examples of possible constraints on the selection process include one or more of minimizing charge injection into the tissue, minimizing spread of the test VOA outside of the target VOA, maximizing overlap between the test VOA and target VOA, limiting the stimulus amplitude to being greater than −10 V and less then 10V, limiting the stimulus pulse duration to being greater than 0 and less than 450 ms, limiting the stimulation frequency to being greater than 0 and less than 185 Hz. In one such example, limits on the stimulation parameters are determined by the output of the current clinical stimulator. Therefore, if new technology provides new output limits, our model limits could be refined to reflect these changes. In a further example, the engineering optimization uses one or more penalty functions, which can be applied for test VOAs that spread into neighboring anatomical structures that are known to induce side effects.

When using PSNSMS pre-operatively, in one example, both the electrode location and stimulation parameters can be varied to determine test VOAs that match the target VOA. This helps determine a pre-operative target for stereotactic neurosurgical implantation of the electrode.

When using PSNSMS post-operatively, in one example, the modeled electrode position in the tissue medium is established using the actual implanted electrode location. Then, one or more stimulation parameters are varied to determine test VOAs, which are compared to the target VOA to determine which test VOA (and hence, which parameter setting(s)) obtain the closest match to the target VOA. This indicates which chronic stimulation parameter settings maximize or otherwise provide the desired therapeutic benefit.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description, and aspects of described methods will be computer-implementable as instructions on a machine-accessible medium. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. A computer-assisted method comprising:
    obtaining imaging data of an anatomic volume of a brain of a patient;
    obtaining nonuniform tissue conductivity data of the anatomic volume to represent inhomogeneous and anisotropic tissue properties;
    creating a finite element model (FEM) of a tissue volume near a possible electrode location, in which the FEM is tailored to a particular electrode morphology, and in which the FEM incorporates the nonuniform tissue conductivity data;
    solving the FEM, by a computer processor, to obtain a second difference in an electric potential distribution in the tissue volume;
    defining at least one threshold requirement on the second difference in the electric potential distribution, including using at least one neuron or axon model to define the at least one threshold requirement; and
    computing, by the computer processor, a volume of influence defined by a surface about the possible electrode location at which the second difference in the electric potential distribution meets the threshold requirement.

2. The method of claim 1, further including selecting a desired electrode location by comparing the computed volume of influence to a desired volume of influence.

3. The method of claim 2, further including positioning an electrode at the selected desired electrode location.

4. The method of claim 1, further including selecting a desired stimulation parameter by comparing the computed volume of influence to a desired volume of influence.

5. The method of claim 4, further including programming an electrical circuit to deliver an electrical stimulation to an electrode using the selected desired stimulation parameter.

6. The method of claim 1, in which the using at least one neuron or axon model to define the at least one threshold requirement includes using an electric field model together with a multi-compartment neuron model oriented and positioned to represent at least one actual nerve pathway in the anatomic volume.

7. The method of claim 1, further comprising:
    displaying, by a display device, the computed volume of influence.

8. The method of claim 1, further comprising:
    displaying, by a display device, the FEM.

9. A computer-assisted method comprising:
creating a finite element model (FEM) of a tissue volume near an electrode location, in which the FEM is tailored to a particular electrode morphology selected from a plurality of candidate electrode morphologies, and in which the FEM incorporates non-uniform tissue conductivity data to represent inhomogeneous and anisotropic tissue properties;
solving the FEM for each candidate electrode morphology, by a computer processor, to compute a volume of influence for each candidate electrode morphology, wherein the volume of influence comprises a predicted volume of tissue affected by an electrical stimulation delivered by each candidate electrode morphology, and wherein computing the volume of influence comprises at least one of:
  i) calculating a second difference of a potential distribution to represent the volume of influence; and
  ii) calculating the volume of influence, wherein the calculating of the volume of influence includes using an electric field model together with a multi-compartment neuron model oriented and positioned to represent at least one actual nerve pathway in the anatomic volume; and
selecting at least one of the candidate electrode morphologies using the volume of influence.

10. The method of claim 9, further comprising manufacturing at least one electrode having the selected at least one of the candidate electrode morphologies.

11. The method of claim 9, further comprising using at least one electrode having the selected at least one of the candidate electrode morphologies to deliver a deep brain stimulation therapy.

12. The method of claim 11, further comprising programming an electrical circuit to deliver an electrical stimulation using the selected at least one of the candidate electrode morphologies, the programming including using at least one simulation parameter selected using the computed volume of influence.

13. The method of claim 9, wherein computing the volume of influence comprises calculating a second difference of a potential distribution to represent the volume of influence.

14. The method of claim 9, wherein computing the volume of influence comprises calculating the volume of influence using an electric field model together with a multi-compartment neuron model oriented and positioned to represent at least one actual nerve pathway in the anatomic volume.

15. The method of claim 9, further comprising:
displaying, by a display device, the computed volume of influence.

16. The method of claim 9, further comprising:
displaying, by a display device, the FEM.

17. A patient-specific neurostimulation modeling system comprising:
  a computer-readable medium having stored thereon:
    a volumetric electric field model including non-uniform conductivity data to represent inhomogeneous and anisotropic tissue properties of a tissue region of a patient; and
    at least one neuron or axon model that specifies a position of neurons within the region according to at least one patient-specific neural pathway;
  a processor that is configured to calculate a volume of influence by solving at least one of:
    i) a second difference of a potential distribution to represent the volume of influence; and
    ii) an electric field model together with a multi-compartment neuron model oriented and positioned to represent at least one actual nerve pathway in the anatomic volume;
  an imaging display that is configured to display volumetric imaging data of the region together with the calculated volume of influence; and
  a correlation or optimization module that is configured to assist in the selection of at least one of a desired electrode location and at least one desired stimulation parameter setting using the volume of influence.

18. The system of claim 17, in which the electric field model includes a finite element model (FEM) mesh that is particular to an electrode morphology and that permits a non-uniform tissue conductivity in the region.

19. The system of claim 17, in which the at least one neuron or axon model includes a multi-compartment electrical model.

20. A computer-assisted method comprising:
creating a finite element model (FEM) of a tissue volume near a possible electrode location, in which the FEM is tailored to a particular electrode morphology;
solving the FEM, by a computer processor, to obtain a second difference in an electric potential distribution in the tissue volume;
defining at least one threshold requirement on the second difference in the electric potential distribution, including using at least one neuron or axon model to define the at least one threshold requirement; and
computing, by the computer processor, a volume of influence defined by a surface about the possible electrode location at which the second difference in the electric potential distribution meets the threshold requirement.

21. The method of claim 20, further comprising:
obtaining imaging data of an anatomic volume of a brain of a patient; and
applying to at least one node of the FEM a white matter conductivity tensor and applying to at least one node of the FEM a grey matter conductivity sensor, the conductivity tensors being applied using a co-registration of the FEM with the imaging data.

22. The method of claim 20, further comprising:
obtaining imaging data of an anatomic volume of a brain of a patient covering a plurality of brain regions for which different conductivity tensors are defined, the plurality of brain regions corresponding to a plurality of regions of the FEM;
assigning the conductivity tensors to the FEM in accordance with the correspondence of the FEM regions with the plurality of brain regions.

23. The method of claim 20, further comprising:
providing a correlation or optimization module that assists in a selection of at least one of a desired electrode location and at least one desired stimulation parameter setting using the volume of influence.

24. A computer-assisted method comprising:
creating a finite element model (FEM) of a tissue volume near an electrode location, in which the FEM is tailored to a particular electrode morphology selected from a plurality of candidate electrode morphologies;
solving the FEM for each candidate electrode morphology, by a computer processor, to compute a volume of influence for each candidate electrode morphology, wherein the volume of influence comprises a predicted volume of tissue affected by an electrical stimulation delivered by each candidate electrode morphology, and wherein computing the volume of influence comprises at least one of:

i) calculating a second difference of a potential distribution to represent the volume of influence; and ii) calculating the volume of influence, wherein the calculating of the volume of influence includes using an electric field model together with a multi-compartment neuron model oriented and positioned to represent at least one actual nerve pathway in the anatomic volume; and selecting at least one of the candidate electrode morphologies using the volume of influence.

25. The method of claim 24, further comprising:
applying different conductivity tensors to different nodes of the FEM.

26. The method of claim 24, further comprising:
providing a correlation or optimization module that assists in a selection of at least one of a desired electrode location and at least one desired stimulation parameter setting using the volume of influence.

27. A patient-specific neurostimulation modeling system comprising:

a computer-readable medium having stored thereon:
  a volumetric electric field model; and
  at least one neuron or axon model that specifies a position of neurons within the region according to at least one patient-specific neural pathway;

a processor that is configured to calculate a volume of influence by solving at least one of:
  i) a second difference of a potential distribution to represent the volume of influence; and
  ii) an electric field model together with a multi-compartment neuron model oriented and positioned to represent at least one actual nerve pathway in an anatomic volume;

an imaging display that is configured to display volumetric imaging data of the region together with the calculated volume of influence; and a correlation or optimization module that is configured to assist in the selection of at least one of a desired electrode location and at least one desired stimulation parameter setting using the volume of influence.

28. The system of claim 27, wherein different conductivity tensors are applied to different nodes of the volumetric electric field.

* * * * *